Figure 1:
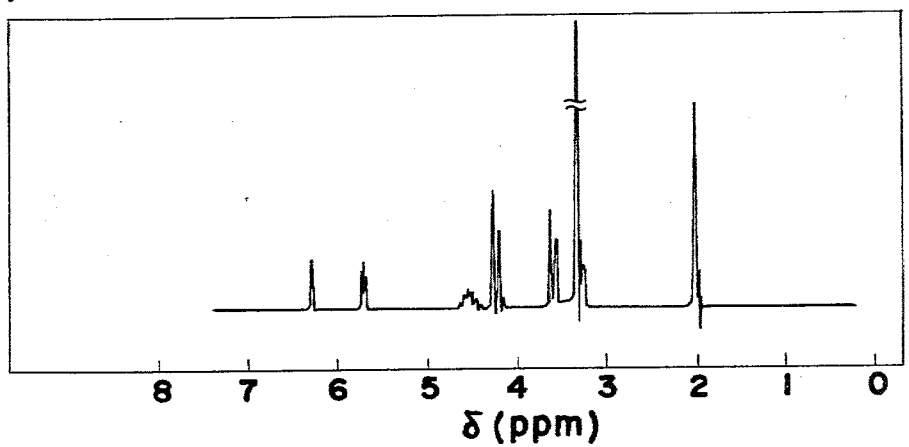

United States Patent [19]

Mizuguchi et al.

[11] 4,238,609
[45] Dec. 9, 1980

[54] PRODUCTION OF AMPHO-IONIC COMPOUNDS

[75] Inventors: Ryuzo Mizuguchi; Atsushi Takahashi; Shinichi Ishikura; Akimitsu Uenaka, all of Osaka, Japan

[73] Assignee: Nippon Paint Co., Ltd., Osaka, Japan

[21] Appl. No.: 966,045

[22] Filed: Dec. 4, 1978

[30] Foreign Application Priority Data

| Dec. 3, 1977 [JP] | Japan | 52-146416 |
| Dec. 28, 1977 [JP] | Japan | 52-159788 |
| Dec. 28, 1977 [JP] | Japan | 52-159789 |
| Mar. 24, 1978 [JP] | Japan | 53-34649 |
| Mar. 24, 1978 [JP] | Japan | 53-34650 |

[51] Int. Cl.³ ............... C07D 245/08; C07C 137/00
[52] U.S. Cl. ........................... 544/158; 546/236; 546/248; 546/339; 546/341; 260/401; 260/456 NS
[58] Field of Search ............... 560/222; 260/456 NS, 260/401; 544/158; 546/248, 339, 341, 236

[56] References Cited

U.S. PATENT DOCUMENTS 3,184,477  5/1965  Baird et al. ............ 260/456 NS

FOREIGN PATENT DOCUMENTS 742541  12/1969  Belgium ............ 260/456 NS

*Primary Examiner*—Henry R. Jiles
*Assistant Examiner*—R. W. Ramsuer
*Attorney, Agent, or Firm*—Wenderoth, Lind & Ponack

[57] ABSTRACT

Ampho-ionic compounds of the formula

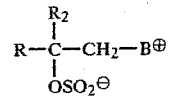

wherein, for example, R is $CH_2=C(CH_3)-COOCH_2-$, $R_2$ is hydrogen and $B^\oplus$ is $-N^\oplus-(CH_3)_2C_{12}H_{25}$, are prepared by reacting an oxirane compound with sulfur dioxide and a tertiary amine. These ampho-ionic compounds are useful as, for example, surfactants.

6 Claims, 33 Drawing Figures

PRODUCTION OF AMPHO-IONIC COMPOUNDS

The present invention relates to novel amphoionic compounds and their production. More particularly, it relates to novel ampho-ionic compounds which have a cationic group and an anionic group in the form of an inner salt, possess characteristic chemical reactivity, surface activity and electrochemical property and optionally include one or more polymerizable unsaturated groups, and their production.

The ampho-ionic compounds of the present invention are representable by the formula:

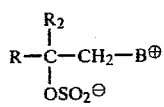 (I)

wherein R is (i) a group of the formula:

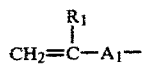

wherein $R_1$ is hydrogen or methyl and $A_1$ is —COOCH$_2$—, —CH$_2$OCH$_2$— or —CONHCH$_2$—, or (ii) a substituent comprising as the major constituent a hydrocarbon chain having 8 to 30 carbon atoms;

$R_2$ is hydrogen or methyl; and
when R is the group (i),

B⊕ is (a) a group of any one of the formulas:

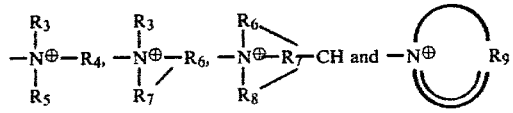

wherein $R_3$, $R_4$ and $R_5$ are each alkyl, alkenyl, hydroxyalkyl, mercaptoalkyl, alkoxy, alkylthio, cyclic alkyl, phenyl or substituted phenyl, each of these groups having not more than 7 carbon atoms, $R_6$, $R_7$ and $R_8$ are each alkylene, alkenylene, alkyleneoxy or alkylenethio, each of these groups having not more than 7 carbon atoms, and $R_9$ is optionally substituted alkylidene of 4 to 10 carbon atoms, (b) a group of the formula:

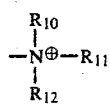

wherein $R_{10}$, $R_{11}$ and $R_{12}$ are each a substituent comprising as the major constituent a hydrocarbon chain having 10 to 30 carbon atoms or when two or three of them are combined together, they represent a heterocyclic group, or (c) a group of the formula:

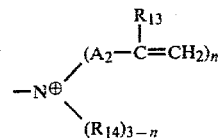

wherein $R_{13}$ is hydrogen or methyl, $R_{14}$ is a substituent comprising as the major constituent a hydrocarbon chain having 1 to 20 carbon atoms, $A_2$ is —(CH$_2$)$_m$OCO—, —(CH$_2$)$_m$NHCO— or —(CH$_2$)$_m$— or when taken together with a part or the whole of $R_{14}$, forms a heterocyclic structure, m is an integer of 1 to 4 and n is an integer of 1 to 3; or when R is the substituent (ii), B⊕ is (d) a group of the formula:

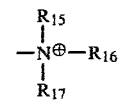

wherein $R_{15}$, $R_{16}$ and $R_{17}$ are each a substituent comprising as the major constituent a hydrogen group having 3 to 8 carbon atoms and possessing no polymerizability or when two or three of them are combined together, they represent a heterocyclic group, (e) a group of the formula:

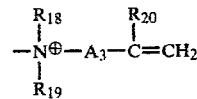

wherein $R_{18}$ and $R_{19}$ are each a substituent comprising as the major constituent a hydrocarbon group having 2 to 7 carbon atoms, $R_{20}$ is hydrogen or methyl and $A_3$ is —COO(CH$_2$)$_p$—, —CONH(CH$_2$)$_p$— or —(CH$_2$)$_p$—, or when taken together with $R_{18}$ or with $R_{18}$ and $R_{19}$, forms a heterocyclic structure and p is an integer of 1 to 3, or (f) a group of the formula:

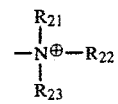

wherein $R_{21}$, $R_{22}$ and $R_{23}$ are each a substituent comprising as the major constituent a hydrocarbon chain having 10 to 30 carbon atoms or when two or three of them are taken together, they represent a heterocyclic group.

Among the ampho-ionic compounds (I), there are included the compounds of the formulas:

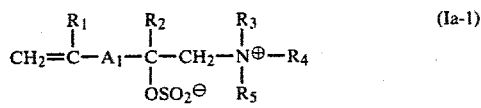 (Ia-1)

-continued

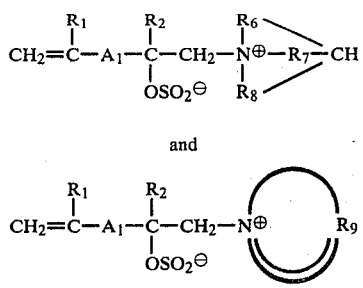
(Ia-2)

(Ia-3)

and (Ia-4)

wherein $A_1$, $R_1$, $R_2$, $R_3$, $R_4$, $R_5$, $R_6$, $R_7$, $R_8$ and $R_9$ are each as defined above.

There are also included the compounds of the formula:

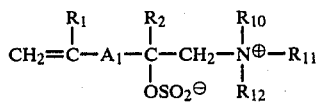
(Ib)

wherein $A_1$, $R_1$, $R_2$, $R_{10}$, $R_{11}$ and $R_{12}$ are each as defined above.

There are further included the compounds of the formula:

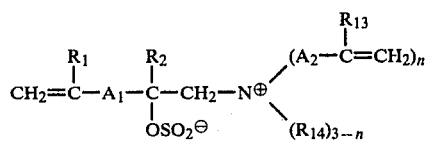
(Ic)

wherein $A_1$, $A_2$, $R_1$, $R_2$, $R_{13}$, $R_{14}$ and n are each as defined above.

There are further included the compounds of the formula:

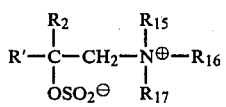
(Id)

wherein R' is a substituent comprising as the major constituent a hydrocarbon chain having 8 to 30 carbon atoms, and $R_2$, $R_{15}$, $R_{16}$ and $R_{17}$ are each as defined above.

There are further included the compounds of the formula:

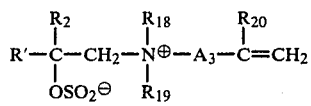
(Ie)

wherein $A_3$, R', $R_2$, $R_{18}$, $R_{19}$ and $R_{20}$ are each as defined above.

There are further included the compounds of the formula:

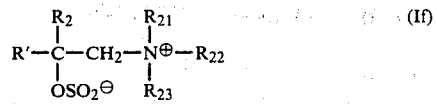
(If)

wherein R', $R_2$, $R_{21}$, $R_{22}$ and $R_{23}$ are each as defined above.

The ampho-ionic compounds (I) are generally produced by reacting an oxirane compound with sulfur dioxide and a tertiary amine.

For instance, the compounds (Ia-1), (Ia-2), (Ia-3), (Ia-4), (Ib) and (Ic) are respectively produced by reacting an oxirane compound of the formula:

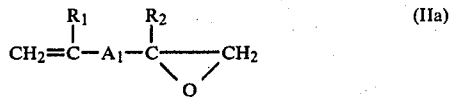
(IIa)

wherein $A_1$, $R_1$ and $R_2$ are each as defined above with sulfur dioxide and a tertiary amine of the formulas:

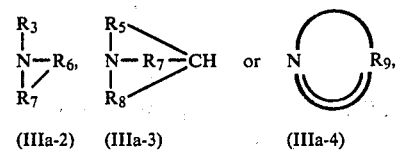

(IIIa-1)　(IIIa-2)　(IIIa-3)　(IIIa-4)

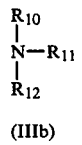

(IIIb)

or

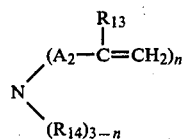

(IIIc)

wherein $A_2$, $R_3$, $R_4$, $R_5$, $R_6$, $R_7$, $R_8$, $R_9$, $R_{10}$, $R_{11}$, $R_{12}$, $R_{13}$, $R_{14}$ and n are each as defined above.

Examples of the oxirane compound (IIa) are glycidyl or methylglycidyl acrylate, glycidyl or methylglycidyl methacrylate, allyl glycidyl or methylglycidyl ether, methallyl glycidyl or methylglycidyl ether, glycidyl or methylglycidyl derivative of acrylamide, glycidyl or methylglycidyl derivative of methacrylamide, etc.

As the amine (IIIa-1), there are exemplified trimethylamine, triethylamine, methyldiethylamine, dimethylethylamine, dimethylbutylamine, dimethylhexylamine, dimethylethanolamine, dimethylbutanolamine, methyldiethanolamine, triethanolamine, dimethyl(2-methoxyethyl)amine, dimethylthioethanolamine, dimethylcyclohexylamine, N,N-dimethylaniline, dimethyl(p-methylphenyl)amine, etc. Examples of the amine (IIIa-2) are N-methylaziridine, N-methylpyrrolidine, N-methylpiperidine, N-ethylpiperidine, N-methylmorpholine, N-ethylmorpholine, 4-methyltetrahydrothiazine, etc. Examples of the amine (IIIa-3) include quinuclidine, etc. Examples of the amine (IIIa-4) include pyridine, quinoline, methylpyridine, etc.

As the amine (IIIb), there may be exemplified dimethyloctylamine, dimethyldecylamine, dimethyllaurylamine, dimethylmyristylamine, dimethylpalmitylamine, dimethylstearylamine, methyldioctylamine, methyldidecylamine, methyldilaurylamine, dimethyl(2-hydroxyoctyl)amine, dimethyl(2-hydroxydecyl)amine, dimethyl(2-hydroxydodecyl)amine, dimethyl(2-hydroxyhexadecyl)amine, dimethyl(2-hydroxylauryl)amine, dimethyl(2-hydroxymyristyl)amine, dimethyl(2-hydroxypalmityl)amine, dimethyl(2-hydroxystearyl)amine, methyldi(2-hydroxyoctyl)amine, methyldi(2-hydroxydecyl)amine, methyldi(2-hydroxydodecyl)amine, methyldi(2-hydroxylauryl)amine, etc. In addition, the amine (IIIb) may be a dimethylbenzylamine having a substituent comprising as the major constituent a hydrocarbon chain having 2 to 18 carbon atoms on the benzene ring, a dimethylaniline having a substituent comprising as the major constituent a hydrocarbon chain having 2 to 18 carbon atoms on the benzene ring, a dimethylcyclohexylamine having a substituent comprising as the major constituent a hydrocarbon chain having 2 to 18 carbon atoms on the cyclohexane ring, a pyridine having a substituent comprising as the major constituent a hydrocarbon chain having 5 to 18 carbon atoms on the pyridine ring, an N-methylpyrrolidine having a substituent comprising as the major constituent a hydrocarbon chain having 5 to 18 carbon atoms on the pyrrolidine ring, an N-methylpiperidine having a substituent comprising as the major constituent a hydrocarbon chain having 5 to 18 carbon atoms on the piperidine ring, an N-methylmorpholine having a substituent comprising as the major constituent a hydrocarbon chain having 5 to 18 carbon atoms on the morpholine ring or the like.

The term "a substituent comprising as the major constituent a hydrocarbon chain" used in this specification is intended to mean a straight or branched aliphatic; alicyclic or aromatic hydrocarbon group, optionally having an unsaturated group, a hydroxyl group, an ether linkage, an ester group, a keto group, and/or the like.

As the amine (IIIc), there may be exemplified dimethylaminoethyl acrylate, dimethylaminoethyl methacrylate, diethylaminoethyl acrylate, diethylaminoethyl methacrylate, dimethylaminopropyl acrylate, dimethylaminopropyl methacrylate, dimethylaminoethylacrylamide, dimethylaminoethylmethacrylamide, dimethylallylamine, dimethylmethallylamide, vinylpyridine, N-methylvinylpyrrolidine, N-methylvinylpiperidine, N-methylvinylmorpholine, methyldi(acryloyloxyethyl)amine, methyldi(methacryloyloxyethyl)amine, methyldi(acryloyloxypropyl)amine, methyldi(methacryloyloxypropyl)amine, methyldiallylamine, methyldimethallylamine, tri(acryloyloxyethyl)amine, tri(methacryloyloxyethyl)amine, triallylamine, trimethallylamine, etc.

The compounds (Id), (Ie) and (If) are respectively produced by reacting an oxirane compound of the formula:

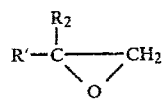

wherein R' and R$_2$ are each as defined above with sulfur dioxide and a tertiary amine of the formulas:

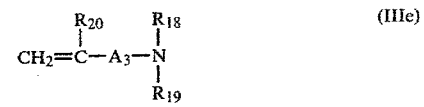

or

wherein A$_3$, R$_{15}$, R$_{16}$, R$_{17}$, R$_{18}$, R$_{19}$, R$_{20}$, R$_{21}$, R$_{22}$ and R$_{23}$ are each as defined above.

The oxirane compound (IIb) includes the following three groups of compounds: (a) the compounds wherein an epoxy ring is directly bonded to a substituent comprising as the major constituent a hydrocarbon chain having 8 to 30 carbon atoms, i.e. the compounds wherein an epoxy is present at the terminal position; (b) the compounds wherein an epoxy ring is bonded to a substituent comprising as the major constituent a hydrocarbon chain having 8 to 30 carbon atoms with an intervention of —OCH$_2$—, i.e. the compounds wherein an epoxy ring is present in the form of a glycidyl ether; and (c) the compounds wherein an epoxy ring is bonded to a substituent comprising as the major constituent a hydrocarbon chain having 8 to 30 carbon atoms with an intervention of —COOCH$_2$—, i.e. the compounds wherein an epoxy ring is present in the form of a glycidyl ester. Specific examples of the oxirane compound (IIb) are as follows: decene oxide, dodecene oxide, tetradecene oxide, hexadecene oxide, octadecene oxide, icocene oxide, dococene oxide, tetracocene oxide, triacontene oxide, octyl glycidyl ether, octyl methylglycidyl ether, decyl glycidyl ether, decyl methylglycidyl ether, tetradecyl glycidyl ether, tetradecyl methylglycidyl ether, hexadecyl glycidyl ether, hexadecyl methylglycidyl ether, octadecyl glycidyl ether, octadecyl methylglycidyl ether, icocyl glycidyl ether, icocyl methylglycidyl ether, dococyl glycidyl ether, dococyl methylglycidyl ether, tetracocyl glycidyl ether, tetracocyl methylglycidyl ether, oleyl glycidyl ether, oleyl methylglycidyl ether, 2-ethylhexyl glycidyl ether, 2-ethylhexyl methylglycidyl ether, cyclohexyl glycidyl ether and its derivatives (e.g. 4-methylcyclohexyl glycidyl ether), cyclohexyl methylglycidyl ether and its derivatives (e.g. 4-methylcyclohexyl methylglycidyl ether), phenyl glycidyl ether and its derivatives, (e.g. o-sec-butylphenyl glycidyl ether, p-nonylphenyl glycidyl ether), phenyl methylglycidyl ether and its derivatives, (e.g. o-sec-butylphehyl methylglycidyl ether, p-nonylphenyl methylglycidyl ether), glycidyl caprate, methylglycidyl caprate, glycidyl laurate, methylglycidyl laurate, glycidyl myristate, methylglycidyl myristate, glycidyl palmitate, methylglycidyl palmitate, glycidyl stearate, methylglycidyl stearate, glycidyl arachidate, methylglycidyl arachidate, glycidyl behenate, methylglycidyl behenate, glycidyl versatate, methylglycidyl versatate, glycidyl oleate, methylglycidyl oleate, glycidyl licinoleate, methylglycidyl licinoleate, glycidyl linoleate, methylglycidyl linoleate, glycidyl linolenate, methylglycidyl linolenate, glycidyl eleostearate, methylglycidyl eleostearate, glycidyl t-nonanoate, methylglycidyl t-nonanoate, glycidyl t-decanoate, methylglycidyl t-decanoate, etc.

As the amine (IIId), there may be exemplified trimethylamine, triethylamine, methyldiethylamine, dimethylethylamine, dimethylpropylamine, dimethylbutylamine, dimethylethanolamine, dimethylbutanolamine, methyldiethanolamine, triethanolamine, dimethyl(2-methoxyethyl)amine, dimethylthioethanolamine, dimethylcyclohexylamine, N-methylaziridine, N-methylpyrrolidine, N-methylpiperidine, N-ethylpiperidine, N-methylmorpholine, N-ethylmorpholine, quinuclidine, pyridine, etc.

Examples of the amine (IIIe) are dimethylaminoethyl acrylate, dimethylaminoethyl methacrylate, diethylaminoethyl acrylate, diethylaminoethyl methacrylate, dimethylaminopropyl acrylate, dimethylaminopropyl methacrylate, dimethylaminoethylacrylamide, dimethylaminoethylmethacrylamide, dimethylallylamine, dimethylmethallylamine, vinylpyridine, N-vinylpyrrolidine, N-vinylpiperidine, N-vinylmorpholine, etc.

Examples of the amine (IIIf) are dimethyloctylamine, dimethyldecylamine, dimethyllaurylamine, dimethylmyristylamine, dimethylpalmitylamine, dimethylstearylamine, methyldioctylamine, methyldidecylamine, methyldilaurylamine, dimethyl(2-hydroxyoctyl)amine, dimethyl(1-hydroxydecyl)amine, dimethyl(2-hydroxydodecyl)amine, dimethyl(2-hydroxyhexadecyl)amine, dimethyl(2-hydroxylauryl)amine, dimethyl(2-hydroxymyristyl)amine, dimethyl(2-hydroxypalmityl)amine, dimethyl(2-hydroxystearyl)amine, methyldi(2-hydroxyoctyl)amine, methyldi(2-hydroxydecyl)amine, methyldi(2-hydroxydodecyl)amine, methyldi(2-hydroxylauryl)amine, etc.

In both cases, the reaction of the oxirane compound with sulfur dioxide and the tertiary amine may be carried out in the presence or absence of an appropriate solvent under atmospheric or elevated pressure. Examples of the appropriate solvent are methanol, ethanol, ethyleneglycol monomethyl ether, acetonitrile, benzene, dimethylsulfoxide, dimethylformamide, etc. The proportion of the oxirane compound, sulfur dioxide and the tertiary amine may be usually in a equivalent molar ratio. The reaction temperature is usually from $-40°$ to $200°$ C., preferably from $-20°$ to $100°$ C. The reaction time is ordinarily from 10 minutes to 100 hours, favorably from 30 minutes to 10 hours. Although no limitation is present on the reaction mode, it is usually preferred first to mix the oxirane compound and sulfur dioxide, if desired, in an appropriate solvent and then to add the tertiary amine to the resulting mixture. If necessary, a polymerization inhibitor such as hydroquinone may be introduced into the reaction system for prevention of the undesirable polymerization of polymerizable unsaturated groups.

The ampho-ionic compounds (I) of the invention have a cationic group ($-N\equiv^\oplus$) and an anionic group ($-OSO_2^\ominus$) separately in their molecules and exert generally advantageous properties due to those groups. Further, they exhibit various characteristics in chemical reactivity, surface activity, electrochemical property and biochemical property. In addition, each of those compounds shows specific and peculiar properties.

For instance, the compounds (Ia-1), (Ia-2), (Ia-3) and (Ia-4) obtained in the form of solid, semi-solid or viscous liquid can be and are generally hygroscopic. They may be used as monomers for production of high polymeric materials, which are provided with said advantageous properties.

The compounds (Ib) have a hydrocarbon group which is hydrophobic and an ammonium group and a sulfite group which are hydrophilic in their molecules, and therefore they exhibit a function as a surfactant. Further, they do not have any low molecular counter ion while they are amphoionic. Because of this reason, they show characteristic surface activity, particularly favorable in emulsion polymerization. In other words, they can serve not only as a monomeric component but also as a surfactant in emulsion polymerization.

The compounds (Ic) are ampho-ionic and have a high stability. They are water-soluble or water-dispersible and can be used as a crosslinking agent in paint compositions, adhesive compositions and plastic compositions comprising water-soluble or water-dispersible resins.

The compounds (Id), (Ie) and (If) have a hydrocarbon group which is hydrophobic and an ammonium group and a sulfite group which are hydrophilic and are therefore useful as a surfactant. Since no low molecular counter ion is present, they are used characteristically in various fields.

Practical and presently preferred embodiments of this invention are illustratively shown in the following Examples.

EXAMPLE 1

In a reactor equipped with a stirrer, glycidyl methacrylate (245.5 g; 1.73 mol) and hydroquinone (0.49 g) are charged while cooling at $-50°$ C., and sulfur dioxide (110.5 g; 1.73 mol) is added thereto while maintaining the temperature of the system below $-20°$ C. Then, trimethylamine (102 g; 1.73 mol) is introduced therein while maintaining the temperature of the system below $-20°$ C. Thereafter, the temperature of the system is gradually elevated up to 75° C. so as to effect the reaction. The reaction is completed in 100 minutes. The reaction product having the following structure is obtained as white solid:

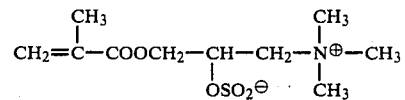

The NMR chart of the said product obtained by the use of an apparatus (100 MHz) manufactured by Nippon Denshi Co., Ltd. and using $d_4$-methanol as a solvent is shown in FIG. 1 of the accompanying drawings.

EXAMPLE 2

In the same manner as in Example 1, allyl glycidyl ether (76.4 g; 0.67 mol), sulfur dioxide (46.1 g; 0.72 mol) and trimethylamine (42.5 g; 0.72 mol) are subjected to reaction in the presence of hydroquinone (0.15 g) at 75° C., the reaction is completed in 100 minutes. The reaction product having the following structure is obtained as pale brown solid:

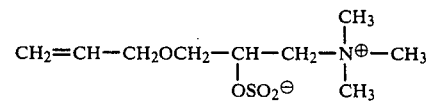

Figure 2:
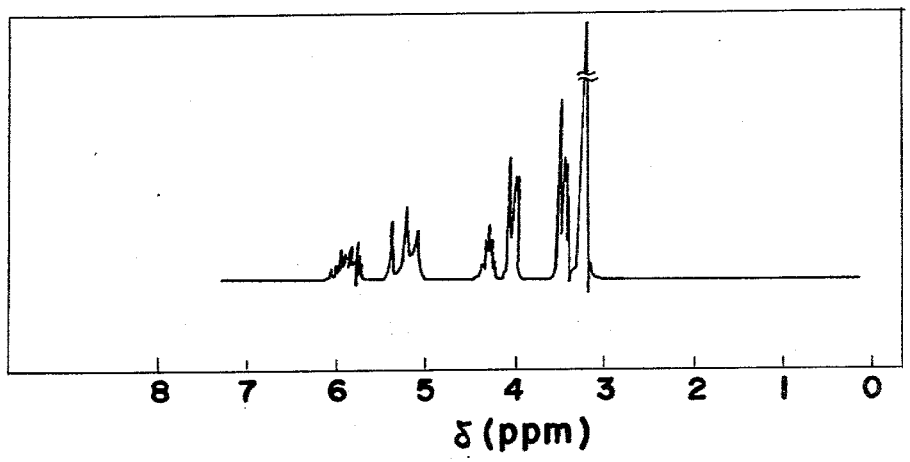

The NMR chart of the said product obtained as in Example 1 is shown in FIG. 2.

EXAMPLE 3

In the same manner as in Example 1, glycidyl methacrylate (164 g; 1.15 mol), sulfur dioxide (74 g; 1.16 mol) and dimethylethanolamine (103 g; 1.16 mol) are subjected to reaction in the presence of hydroquinone (0.33 g) at 50° C., the reaction is completed in 200 minutes. The reaction product having the following structure is obtained as viscous liquid:

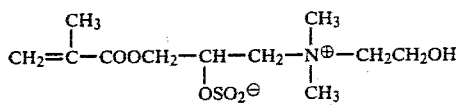

Figure 3:
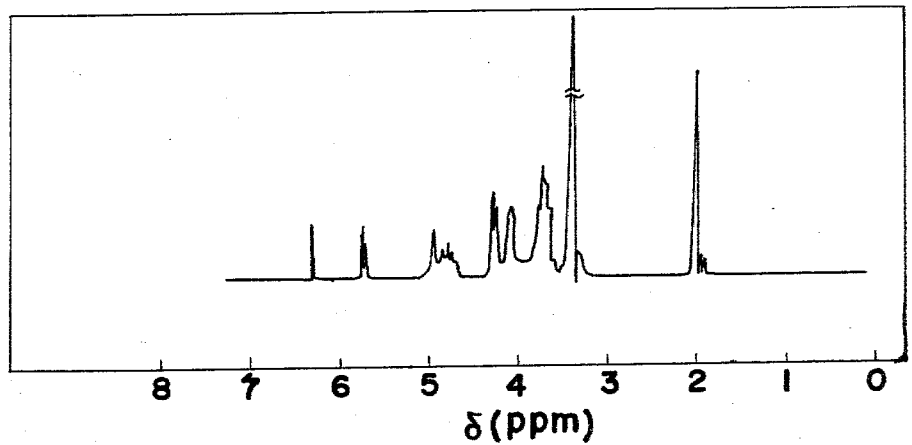

The NMR chart of the said product obtained as in Example 1 is shown in FIG. 3.

EXAMPLE 4

In the same manner as in Example 1, allyl glycidyl ether (136.8 g; 1.2 mol), sulfur dioxide (76.8 g; 1.2 mol) and dimethylethanolamine (106.8 g; 1.2 mol) are subjected to reaction in the presence of hydroquinone (0.3 g) and methanol (38.4 g) at 60° C., the reaction is completed in 200 minutes. The reaction product having the following structure is obtained as pale brown solid:

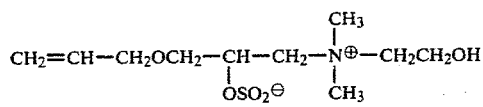

Figure 4:
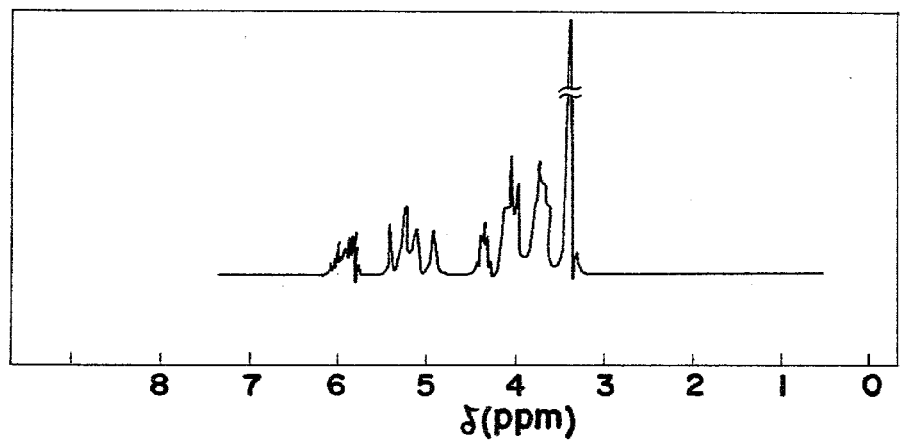

The NMR chart of the said product obtained as in Example 1 is shown in FIG. 4.

EXAMPLE 5

In the same manner as in Example 1, glycidyl methacrylate (113.6 g; 0.8 mol), sulfur dioxide (51.2 g; 0.8 mol) and N-methylpiperidine (79.3 g; 0.8 mol) are subjected to reaction in the presence of hydroquinone (0.23 g) and acetonitrile (65.6 g) at 60° C., the reaction is completed in 200 minutes. The reaction product having the following structure is obtained as white solid:

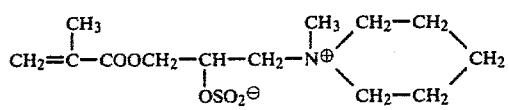

Figure 5:
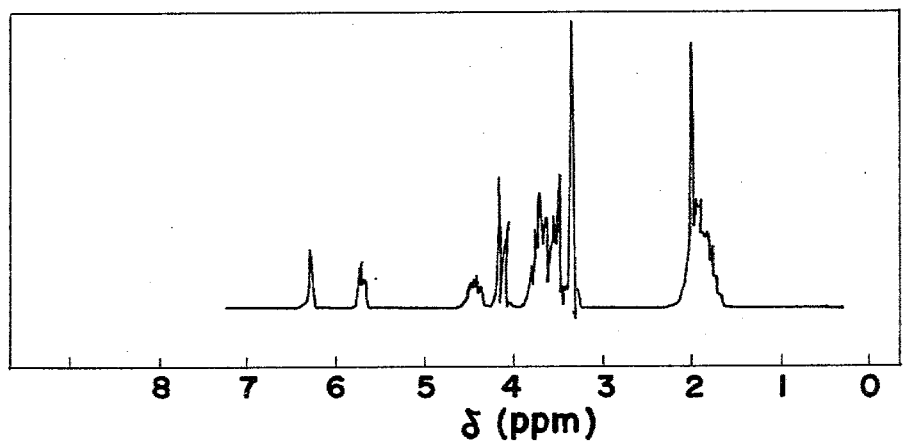

The NMR chart of the said product obtained as in Example 1 is shown in FIG. 5.

EXAMPLE 6

In the same manner as in Example 1, glycidyl methacrylate (113.6 g; 0.8 mol), sulfur dioxide (51.2 g; 0.8 mol) and methyldiethylamine (69.6 g; 0.8 mol) are subjected to reaction in the presence of hydroquinone (0.23 g) at 70° C., the reaction is completed in 150 minutes. The reaction product having the following structure is obtained as pale brown solid:

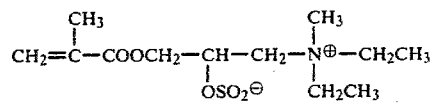

Figure 6:
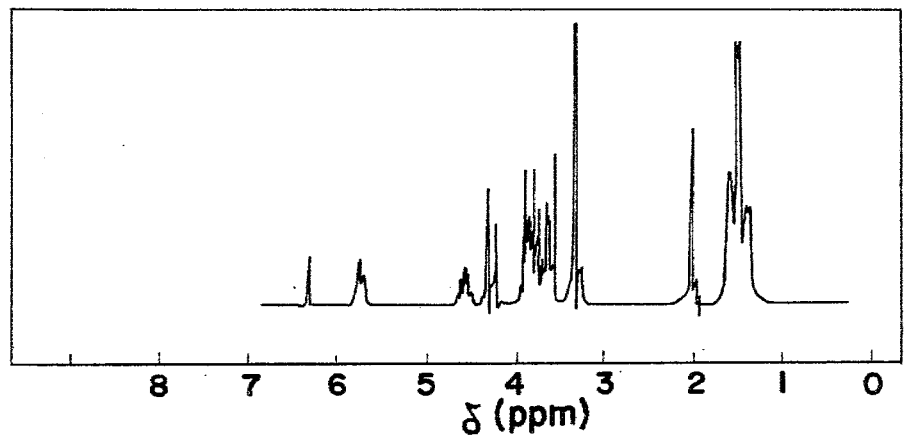

The NMR chart of the said product obtained as in Example 1 is shown in FIG. 6.

EXAMPLE 7

In the same manner as in Example 1, allyl glycidyl ether (125.8 g; 1.1 mol), sulfur dioxide (70.4 g; 1.1 mol) and 4-methylmorpholine (111.3 g; 1.1 mol) are subjected to reaction in the presence of hydroquinone (0.25 g) and ethyleneglycol monomethyl ether (83.7 g) at 70° C., the reaction is completed in 200 minutes. The reaction product having the following structure is obtained as pale brown solid:

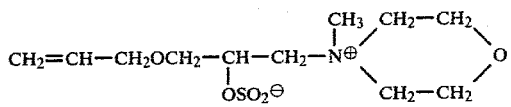

Figure 7:
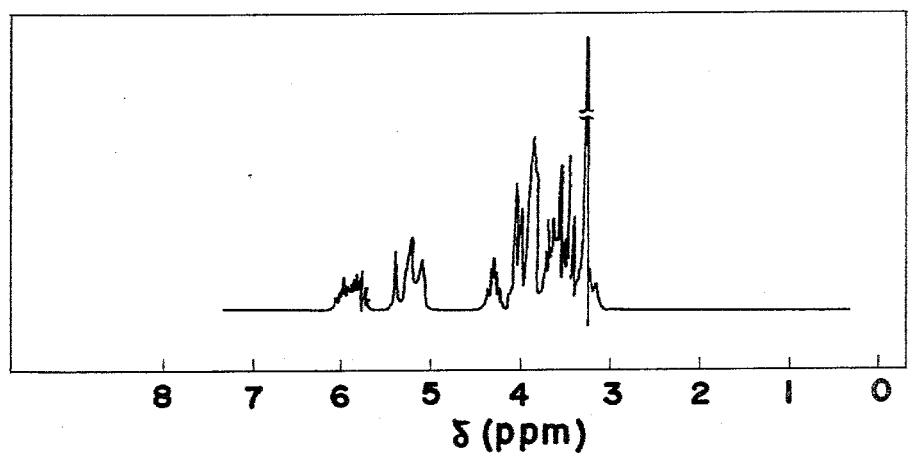

The NMR chart of the said product obtained as in Example 1 is shown in FIG. 7.

EXAMPLE 8

In the same manner as in Example 1, glycidyl methacrylate (124.4 g; 0.875 mol), sulfur dioxide (56 g; 0.875 mol) and triethylamine (88.4 g; 0.875 mol) are subjected to reaction in the presence of hydroquinone (0.25 g) at 70° C., the reaction is completed in 240 minutes. The reaction product having the following structure is obtained as pale brown solid:

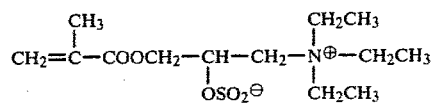

Figure 8:
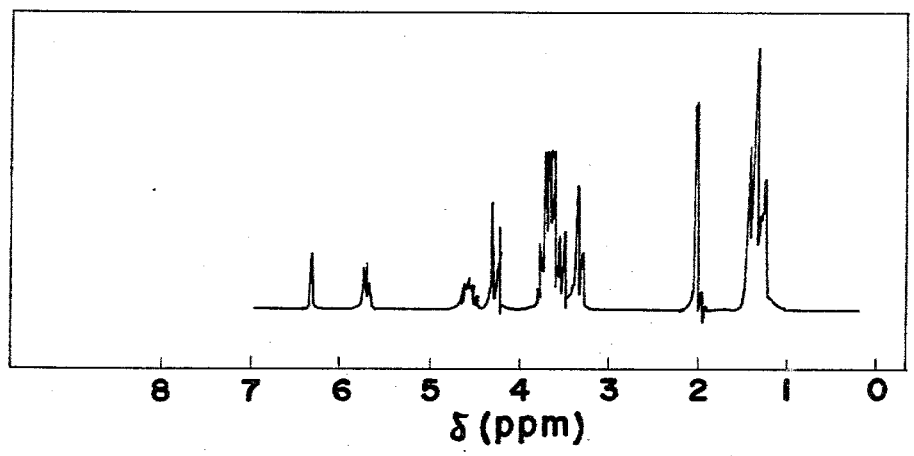

The NMR chart of the said product obtained as in Example 1 is shown in FIG. 8.

EXAMPLE 9

In the same manner as in Example 1, glycidyl methacrylate (118.4 g; 0.833 mol), sulfur dioxide (53.3 g; 0.833 mol) and pyridine (65.9 g; 0.833 mol) are subjected to reaction in the presence of hydroquinone (0.22 g) at 40° C., the reaction is completed in 40 minutes. The reaction product having the following structure is obtained as pale brown solid:

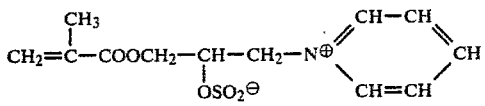

Figure 9:
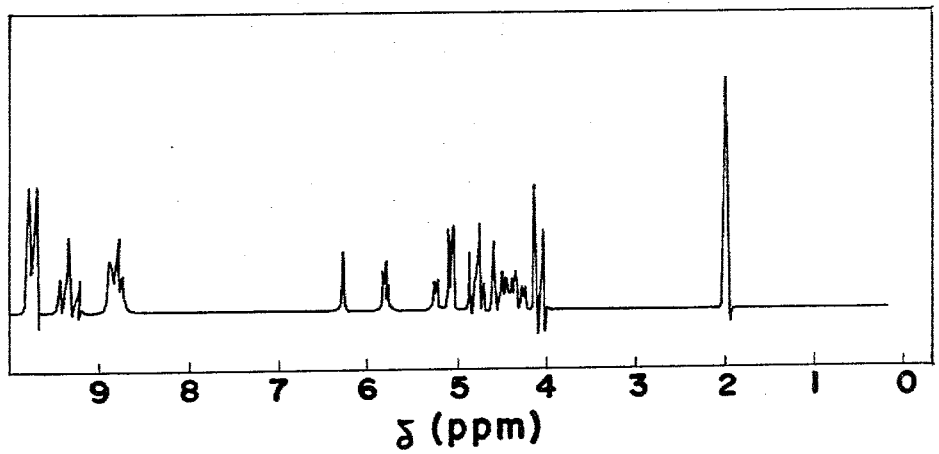

The NMR chart of the said product obtained in Example 1 is shown in FIG. 9.

EXAMPLE 10

In a reactor equipped with a stirrer, glycidyl methacrylate (103.7 g; 0.73 mol) and hydroquinone (0.2 g) are charged while cooling at −50° C., and sulfur dioxide (47.0 g; 0.73 mol) is added thereto while maintaining the temperature of the system below −20° C. Then, dimethyllaurylamine (155.5 g; 0.73 mol) is introduced therein while maintaining the temperature of the system below −20° C. Thereafter, the temperature of the system is gradually elevated up to 70° C. so as to effect the reaction. The reaction is completed in 10 hours. By removal of unreacted materials under reduced pressure, the reaction product having the following structure is obtained as brown cream:

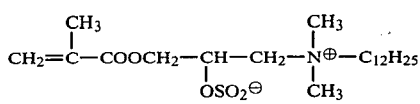

Figure 10:
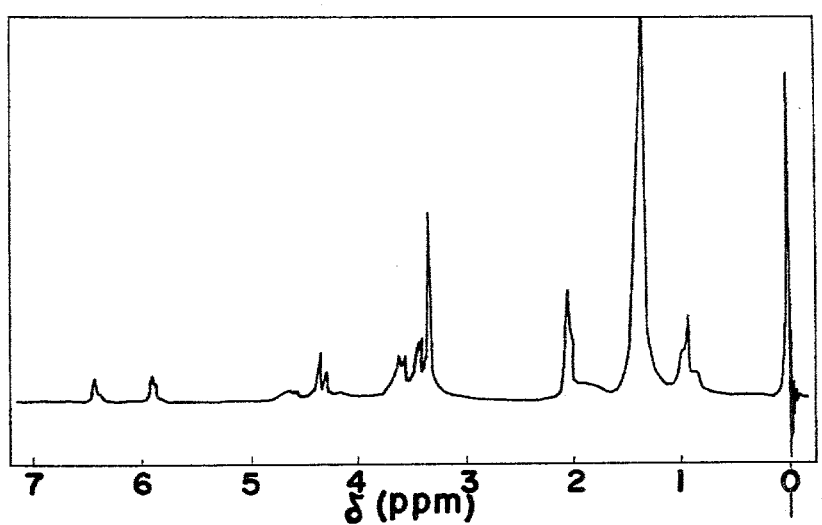

The NMR chart of the said product obtained by the use of an apparatus (100 MHz) manufactured by Nippon Denshi Co., Ltd. and using d$_4$-methanol as a solvent is shown in FIG. 10 of the accompanying drawings. In the IR spectrum, characteristic absorptions are seen at 1040, 3430 and 1630 cm$^{-1}$.

EXAMPLE 11

In the same manner as in Example 10, allyl glycidyl ether (97.0 g; 0.85 mol), sulfur dioxide (54.5 g; 0.85 mol) and dimethyllaurylamine (181.1 g; 0.85 mol) are subjected to reaction in the presence of hydroquinone (0.2 g) and dimethylformamide (40.0 g) at 70° C., the reaction is completed in 8 hours. The reaction product having the following structure is obtained as yellow viscous liquid:

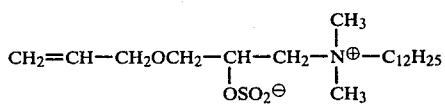

Figure 11:
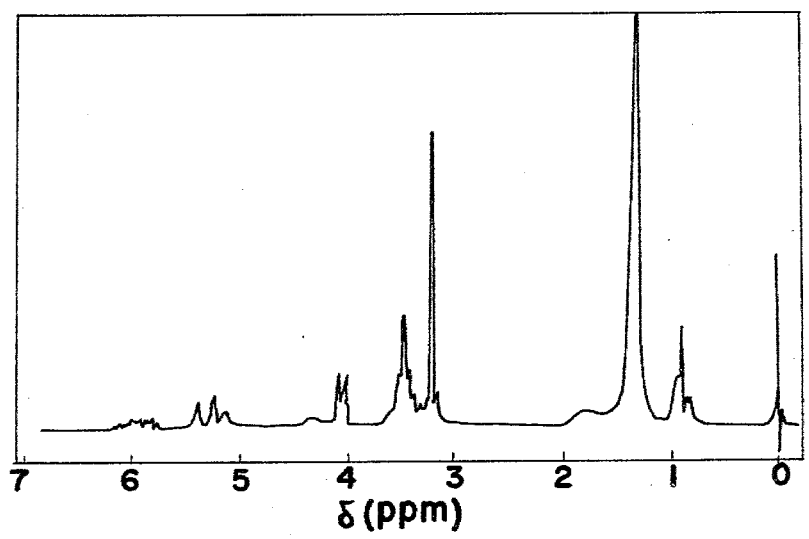

The NMR chart of the said product obtained as in Example 10 is shown in FIG. 11. In the IR spectrum, characteristic absorptions are seen at 1040, 3430 and 1630 cm$^{-1}$.

EXAMPLE 12

In the same manner as in Example 10, glycidyl methacrylate (120.9 g; 0.85 mol), sulfur dioxide (54.5 g; 0.85 mol) and dimethylstearylamine (252.5 g; 0.85 mol) are subjected to reaction in the presence of hydroquinone (0.2 g) at 70° C., the reaction is completed in 8 hours. The reaction product having the following structure is obtained as yellow cream:

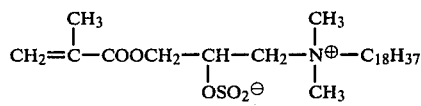

Figure 12:
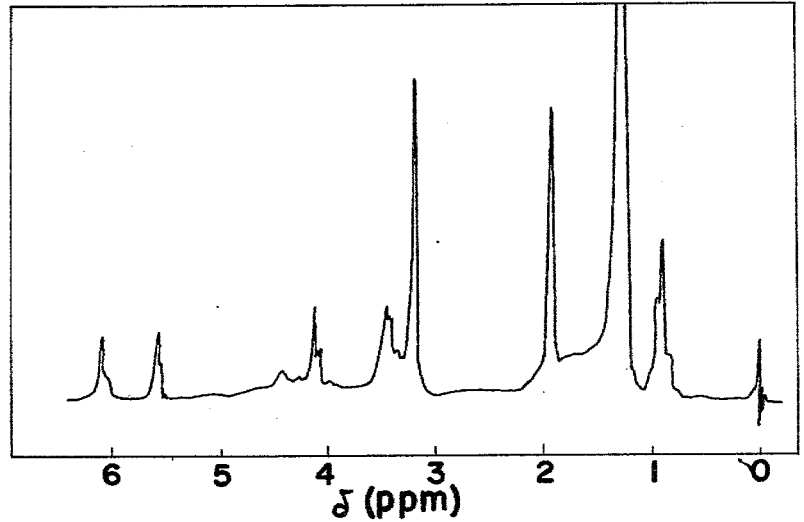

The NMR chart of the said product obtained as in Example 10 is shown in FIG. 12. In the IR spectrum, characteristic absorptions are seen at 1040, 3430 and 1630 cm$^{-1}$.

EXAMPLE 13

In the same manner as in Example 10, allyl glycidyl ether (32.1 g; 0.28 mol), sulfur dioxide (18.0 g; 0.28 mol) and dimethyl(2-hydroxydodecyl)amine (64.1 g; 0.28 mol) are subjected to reaction in the presence of hydroquinone (0.06 g) and ethyleneglycol monomethyl ether (10.7 g) at 70° C., the reaction is completed in 6 hours. The reaction product having the following structure is obtained as pale yellow viscous liquid:

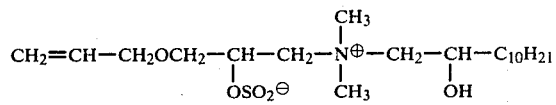

Figure 13:
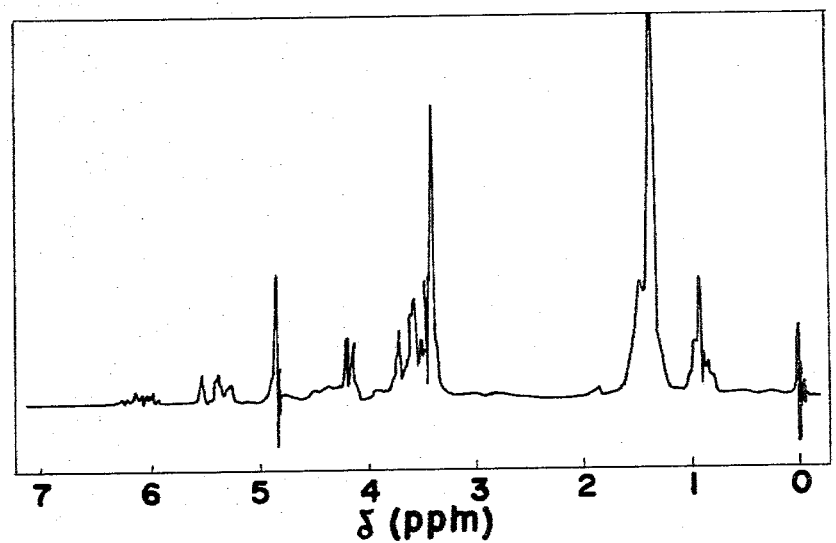

The NMR chart of the said product obtained as in Example 10 is shown in FIG. 13. In the IR spectrum, characteristic absorptions are seen at 1040, 3430 and 1630 cm$^{-1}$.

EXAMPLE 14

In the same manner as in Example 10, glycidyl methacrylate (46.8 g; 0.33 mol), sulfur dioxide (21.1 g; 0.33 mol) and dimethyl(2-hydroxyhexadecyl)amine (103.3 g; 0.33 mol) are subjected to reaction in the presence of hydroquinone (0.1 g) and ethyleneglycol monomethyl ether (50.0 g) at 70° C., the reaction is completed in 8 hours. The reaction product having the following structure is obtained as pale yellow viscous liquid:

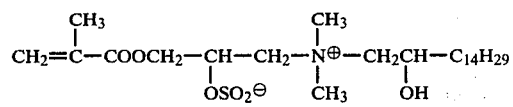

Figure 14:
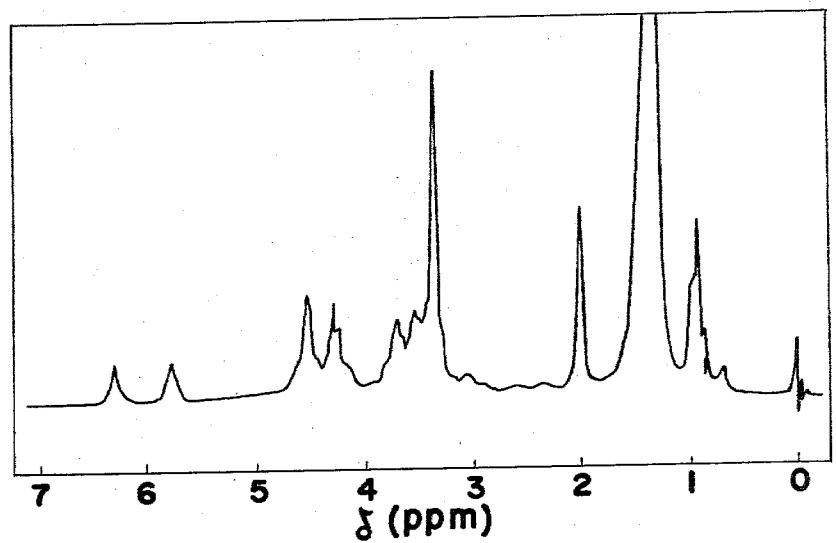

The NMR chart of the said product obtained as in Example 10 is shown in FIG. 14. In the IR spectrum, characteristic absorptions are seen at 1040, 3430 and 1630 cm$^{-1}$.

EXAMPLE 15

In the same manner as in Example 10, glycidyl methacrylate (71.0 g; 0.5 mol), sulfur dioxide (32.0 g; 0.5 mol) and N-dodecylmorpholine (127.5 g; 0.5 mol) are subjected to reaction in the presence of hydroquinone (0.2 g) and dimethylformamide (65 g) at 70° C., the reaction is completed in 8 hours. The reaction product having the following structure is obtained as pale yellow viscous liquid:

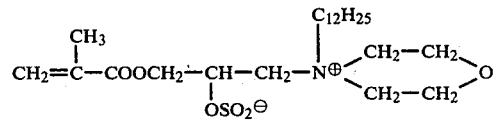

Figure 15:
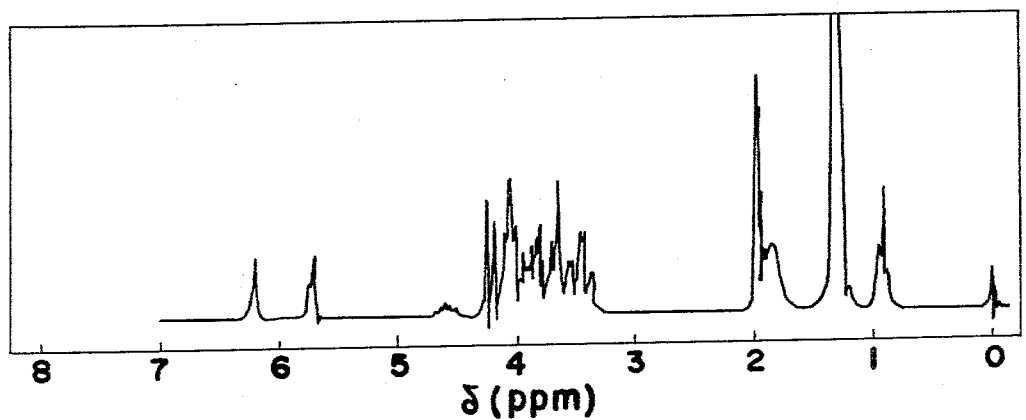

The NMR chart of the said product obtained as in Example 10 is shown in FIG. 15. In the IR spectrum, characteristic absorptions are seen at 1040, 3430 and 1630 cm$^{-1}$.

EXAMPLE 16

In the same manner as in Example 10, allyl glycidyl ether (47.9 g; 0.42 mol), sulfur dioxide (26.9 g; 0.42 mol) and methyldi(2-hydroxydodecyl)amine (167.6 g; 0.42 mol) are subjected to reaction in the presence of hydroquinone (0.1 g) and dimethylformamide (57 g) at 70° C., the reaction is completed in 10 hours. The reaction product having the following structure is obtained as pale yellow viscous liquid:

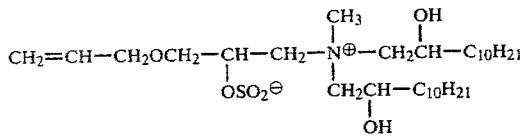

Figure 16:
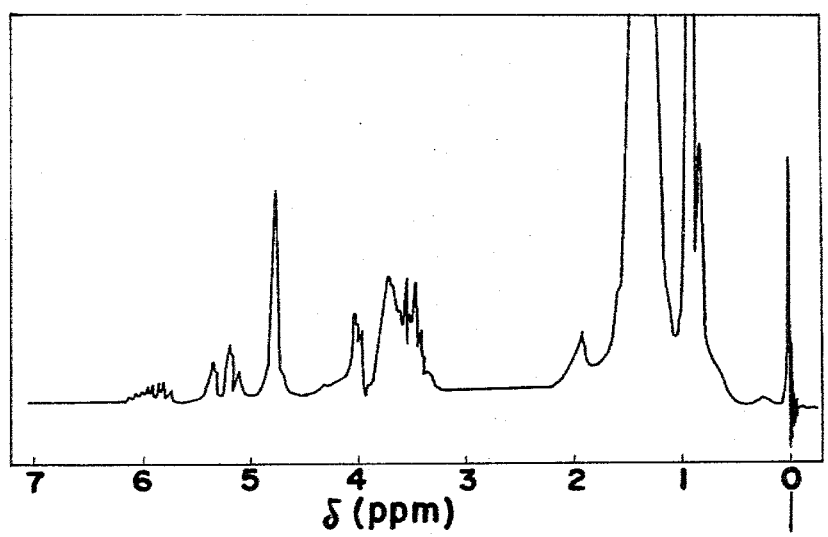

The NMR chart of the said product obtained in Example 10 is shown in FIG. 16. In the IR spectrum, characteristic absorptions are seen at 1040, 3430 and 1630 cm$^{-1}$.

REFERENCE EXAMPLE 1

In a 2 liter volume reactor equipped with a stirrer, a cooler, a temperature controller and an inlet for nitrogen gas, deionized water (450 g) is charged, and the temperature is elevated up to 80° C. while introducing nitrogen gas therein. Potassium persulfate (4.5 g) and sodium hydrogen sulfite (1.5 g) are charged into the reactor, and the reaction product in Example 10 (20 g), methyl methacrylate (124 g), styrene (185 g), n-butyl acrylate (166 g) and laurylmercaptan (5 g) are dropwise added thereto in 30 minutes. Further, potassium persulfate (1.5 g), sodium hydrogen sulfite (0.5 g) and deionized water (70 g) are added thereto, and the reaction is continued for 30 minutes, whereby an emulsion of the produced polymer is obtained.

REFERENCE EXAMPLE 2

In a 2 liter volume reactor equipped with a stirrer, a cooler, a temperature controller and an inlet for nitrogen gas, deionized water (408 g) is charged, and the temperature is elevated up to 80° C. while introducing nitrogen gas therein. An aqueous solution of azobiscyanovaleric acid (8 g) and dimethylethanolamine (4.8 g) is charged into the reactor, and the reaction product in Example 11 (16 g), methyl methacrylate (103 g), styrene (144 g) and n-butyl acrylate (137 g) are dropwise added thereto in 40 minutes. After the dropwise addition is finished, stirring is continued for 30 minutes, whereby an emulsion of the produced polymer is obtained.

EXAMPLE 17

In a reactor equipped with a stirrer, glycidyl methacrylate (44.4 g) and hydroquinone (0.08 g) are charged while cooling at −50° C., and sulfur dioxide (20.0 g) is added thereto while maintaining the temperature of the system below −20° C. Then, dimethylaminoethyl methacrylate (49.1 g) is introduced therein while maintaining the temperature of the system below −20° C. Thereafter, the temperature of the system is gradually elevated up to 60° C. so as to effect the reaction. The reaction is completed in 6 hours. By removal of unreacted materials under reduced pressure, the reaction product having the following structure is obtained as pale yellow liquid:

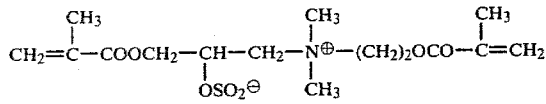

Figure 17:
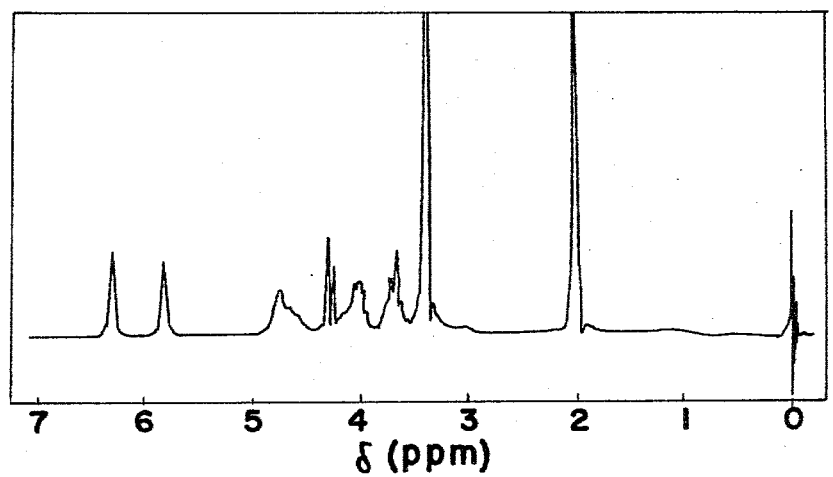

The NMR chart of the said product obtained by the use of an apparatus (100 MHz) manufactured by Nippon Denshi Co., Ltd. and using d$_4$-methanol as a solvent is shown in FIG. 17 of the accompanying drawings. In the IR spectrum, characteristic absorptions are seen at 1040, 3430 and 1630 cm$^{-1}$.

EXAMPLE 18

In the same manner as in Example 17, allyl glycidyl ether (97.1 g), sulfur dioxide (54.5 g) and dimethylaminoethyl methacrylate (133.7 g) are subjected to reaction in the presence of hydroquinone (0.2 g) at 60° C., the reaction is completed in 6 hours. The reaction product having the following structure is obtained:

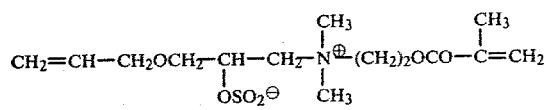

Figure 18:
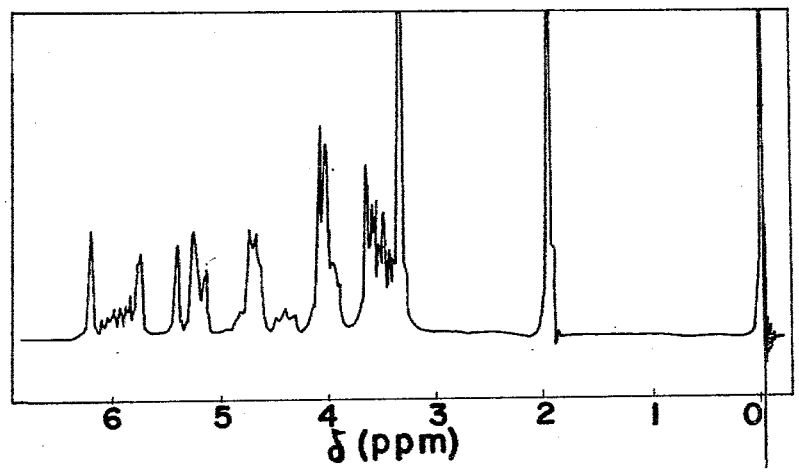

The NMR chart of the said product obtained as in Example 17 is shown in FIG. 18. In the IR spectrum, characteristic absorptions are seen at 1040, 3430 and 1630 cm$^{-1}$.

EXAMPLE 19

In the same manner as in Example 17, glycidyl methacrylate (42.2 g), sulfur dioxide (19 g) and triallylamine (40.7 g) are subjected to reaction in the presence of hydroquinone (0.1 g) and ethyleneglycol monomethyl ether (22.6 g) at 60° C., the reaction is completed in 6 hours. The reaction product having the following structure is obtained:

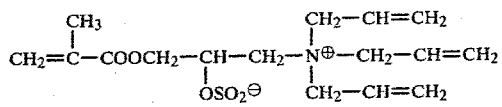

Figure 19:
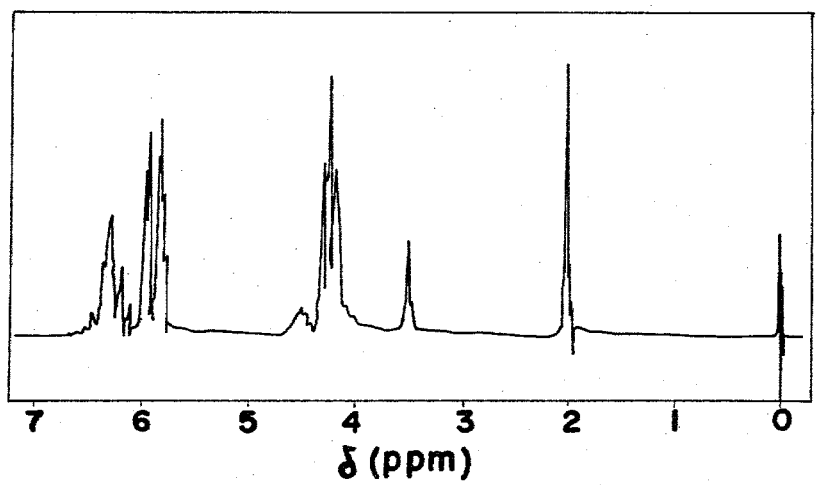

The NMR chart of the said product obtained as in Example 17 is shown in FIG. 19. In the IR spectrum, characteristic absorptions are seen at 1040, 3430 and 1630 cm$^{-1}$.

EXAMPLE 20

In the same manner as in Example 17, allyl glycidyl ether (40.9 g), sulfur dioxide (23.0 g) and triallylamine (49.2 g) are subjected to reaction in the presence of hydroquinone (0.1 g) and ethyleneglycol monomethyl ether (13.7 g) at 60° C., the reaction is completed in 6 hours. The reaction product having the following structure is obtained:

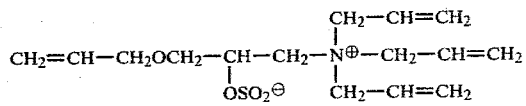

Figure 20:
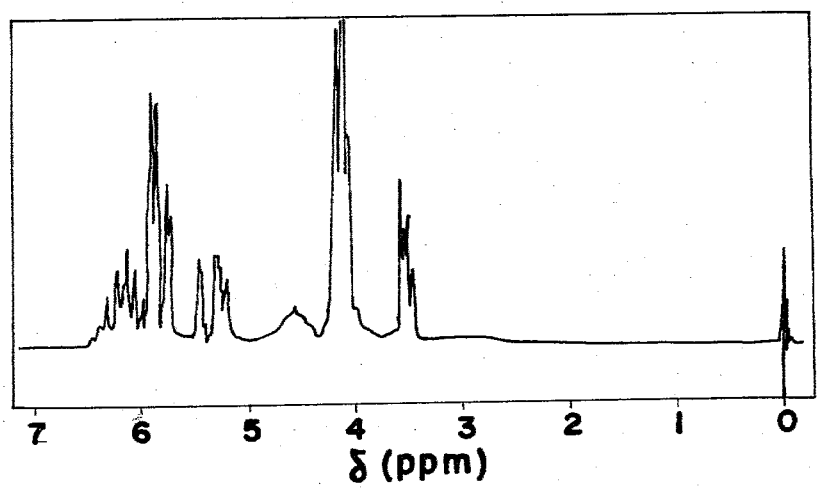

The NMR chart of the said product obtained as in Example 17 is shown in FIG. 20. In the IR spectrum, characteristic absorptions are seen at 1040, 3430 and 1630 cm$^{-1}$.

EXAMPLE 21

In the same manner as in Example 17, allyl glycidyl ether (57.0 g), sulfur dioxide (32.0 g) and 4-vinylpyridine (52.5 g) are subjected to reaction in the presence of hydroquinone (0.1 g) and ethyleneglycol monomethyl ether (40.0 g) at 60° C., the reaction is completed in 6 hours. The reaction product having the following structure is obtained:

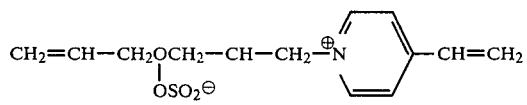

In the NMR analysis, characteristic peaks are recognized at 3.6 δ and 3.6 δ. In the IR spectrum, characteristic absorptions are seen at 1040, 3430 and 1630 cm$^{-1}$.

EXAMPLE 22

In the same manner as in Example 17, glycidyl methacrylate (71.0 g), sulfur dioxide (32.0 g) and dimethylallylamine (42.5 g) are subjected to reaction in the presence of hydroquinone (0.1 g) and dimethylformamide (20 g) at 60° C., the reaction is completed in 6 hours. The reaction product having the following structure is obtained:

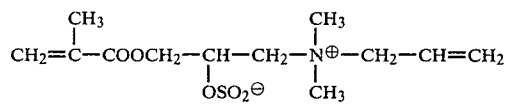

In the NMR analysis, characteristic peaks are recognized at 3.6 δ and 4.6 δ. In the IR spectrum, characteristic absorptions are seen at 1040, 3430 and 1630 cm$^{-1}$.

EXAMPLE 23

In the same manner as in Example 17, allyl glycidyl ether (57.0 g), sulfur dioxide (32.0 g) and dimethylallylamine (42.5 g) are subjected to reaction in the presence of hydroquinone (0.1 g) at 60° C., the reaction is completed in 6 hours. The reaction product having the following structure is obtained:

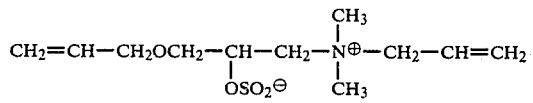

In the NMR analysis, characteristic peaks are recognized at 3.6 δ and 4.6 δ. In the IR spectrum, characteristic absorptions are seen at 1040, 3430 and 1630 cm$^{-1}$.

EXAMPLE 24

In a reactor equipped with a stirrer, 2-ethylhexyl glycidyl ether (66.0 g; 0.355 mol) and ethyleneglycol monomethyl ether (13.5 g) are charged while cooling at −50° C., and sulfur dioxide (22.7 g; 0.355 mol) is added thereto while maintaining the temperature of the system below −20° C. Then, trimethylamine (21.0 g; 0.355 mol) is introduced therein while maintaining the temperature of the system below −20° C. Thereafter, the temperature of the system is gradually elevated up to 70° C. so as to effect the reaction. The reaction is completed in 5 hours. By removal of unreacted materials under reduced pressure, the reaction product having the following structure is obtained as white jelly:

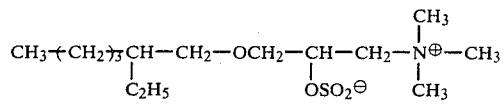

Figure 21:
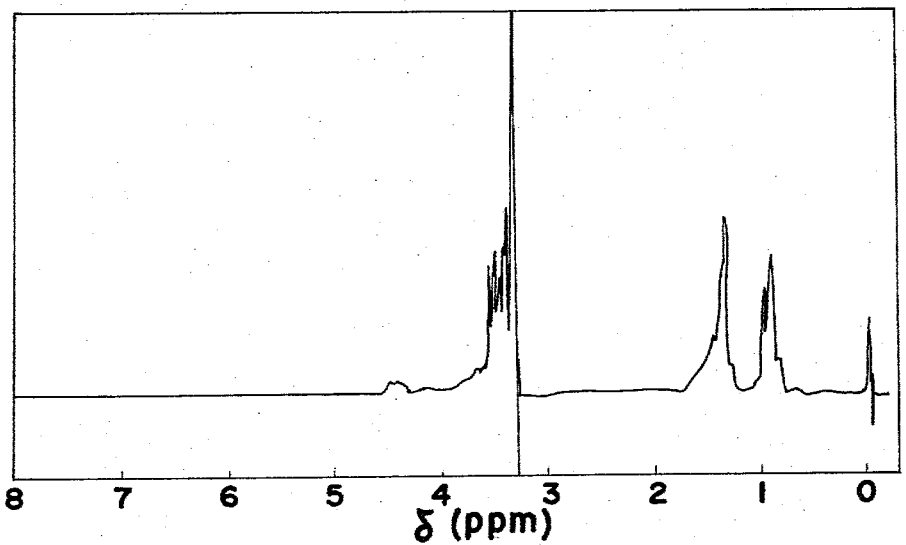

The NMR chart of the said product obtained by the use of an apparatus (100 MHz) manufactured by Nippon Denshi Co., Ltd. and using d$_4$-methanol as a solvent is shown in FIG. 21 of the accompanying drawings. In the IR spectrum, characteristic absorptions are seen at 1040 and 3430 cm$^{-1}$.

EXAMPLE 25

In the same manner as in Example 24, o-sec-butylphenyl glycidyl ether (67.6 g; 0.328 mol), sulfur dioxide (21.0 g; 0.328 mol) and diethylmethylamine (28.5 g; 0.328 mol) are subjected to reaction in the presence of ethyleneglycol monomethyl ether (24.9 g) at 70° C., the reaction is completed in 5 hours. The reaction product having the following structure is obtained as yellow viscous liquid:

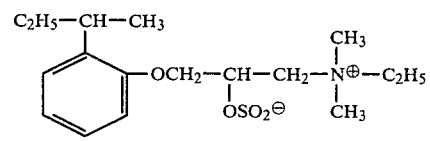

Figure 22:
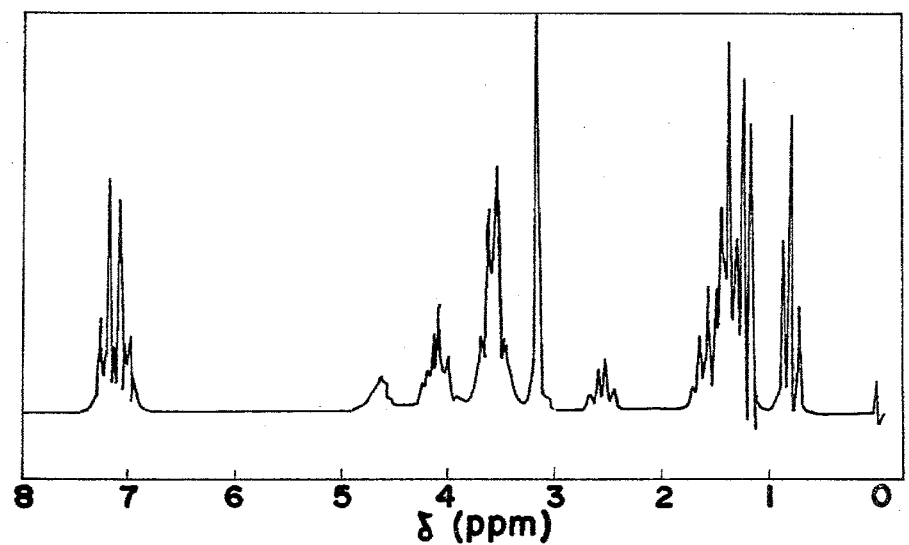

The NMR chart of the said product obtained as in Example 24 is shown in FIG. 22. In the IR spectrum, characteristic absorptions are seen at 1040 and 3430 cm$^{-1}$.

EXAMPLE 26

In the same manner as in Example 24, p-nonylphenyl glycidyl ether (73.4 g; 0.266 mol), sulfur dioxide (17.0 g; 0.266 mol) and N-methylpiperidine (26.4 g; 0.266 mol) are subjected to reaction in the presence of ethyleneglycol monomethyl ether (10.1 g) at 70° C., the reaction is completed in 8 hours. The reaction product having the following structure is obtained as white transparent viscous liquid:

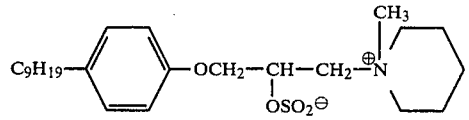

Figure 23:
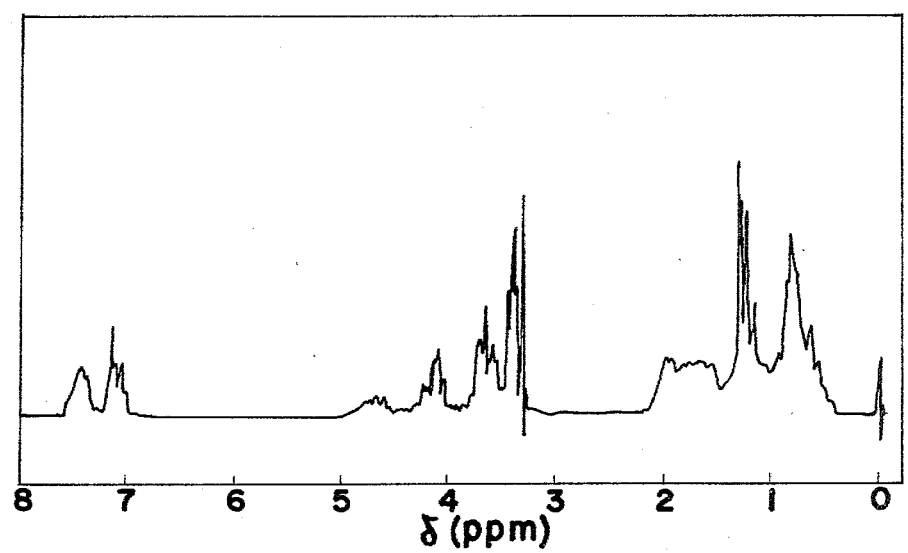

The NMR chart of the said product obtained as in Example 24 is shown in FIG. 23. In the IR spectrum, characteristic absorptions are seen at 1040 and 3430 cm$^{-1}$.

EXAMPLE 27

In the same manner as in Example 24, tetradecene oxide (72.1 g; 0.34 mol), sulfur dioxide (21.8 g; 0.34 mol) and dimethylethanolamine (30.3 g; 0.34 mol) are is subjected to reaction in the presence of dimethylformamide (27.0 g) at 70° C., the reaction is completed in 8 hours. The reaction product having the following structure is obtained as pale yellow viscous liquid:

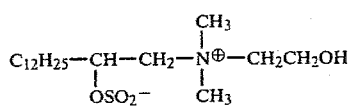

Figure 24:
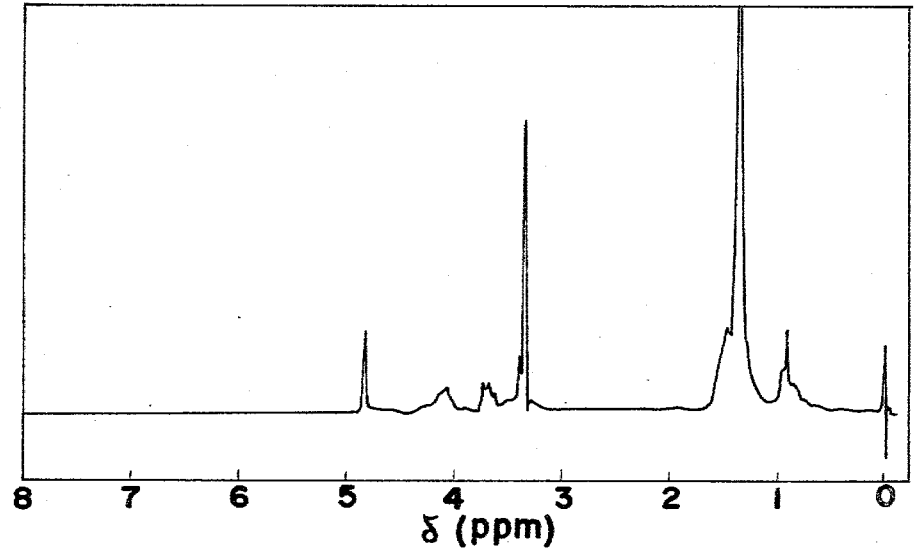

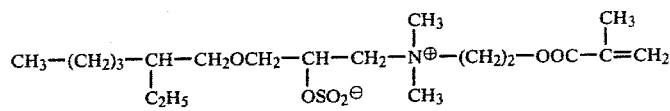

ture of the system is gradually elevated up to 70° C. so as to effect the reaction. The reaction is completed in 6 hours. By removal of unreacted materials under reduced pressure, the reaction product having the following structure is obtained as white cream:

The NMR chart of the said product obtained as in Example 24 is shown in FIG. 24. In the IR spectrum, characteristic absorptions are seen at 1040 and 3430 cm$^{-1}$.

Figure 27:
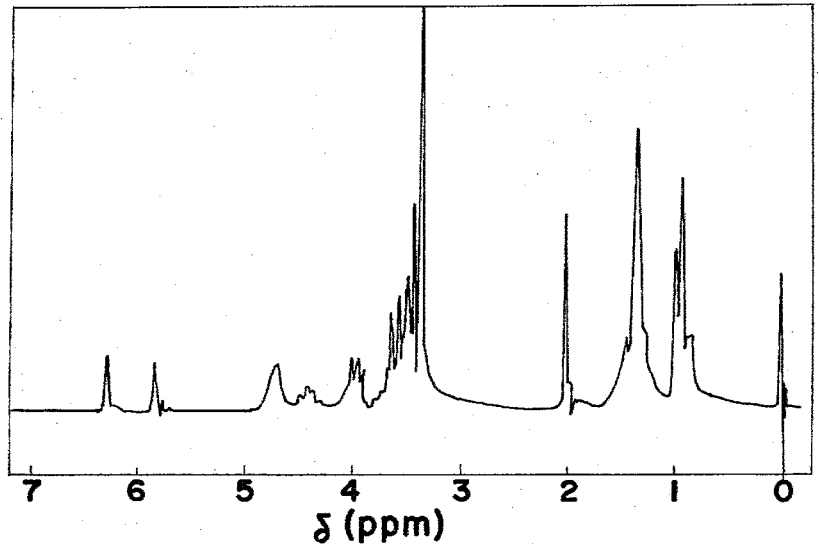

The NMR chart of the said product obtained by the use of an apparatus (100 MHz) manufactured by Nippon Denshi Co., Ltd. and using d$_4$-methanol as a solvent is shown in FIG. 27 of the accompanying drawings. In the IR spectrum, characteristic absorptions are seen at 1040, 3430 and 1630 cm$^{-1}$.

EXAMPLE 28

In the same manner as in Example 24, glycidyl linoleate (67.7 g; 0.195 mol), sulfur dioxide (12.5 g; 0.195 mol) and 4-methylmorpholine (19.7 g; 0.195 mol) are subjected to reaction at 70° C., the reaction is completed in 10 hours. The reaction product having the following structure is obtained as white transparent viscous liquid:

EXAMPLE 31

In the same manner as in Example 30, octadecene oxide (101.0 g; 0.377 mol), sulfur dioxide (24.1 g; 0.377 mol) and dimethylaminoethyl methacrylate (59.1 g; 0.377 mol) are subjected to reaction in the presence of hydroquinone (0.1 g) and acetonitrile (15.4 g) at 70° C., the reaction is completed in 6 hours. The reaction prod-

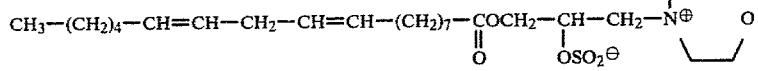

Figure 25:
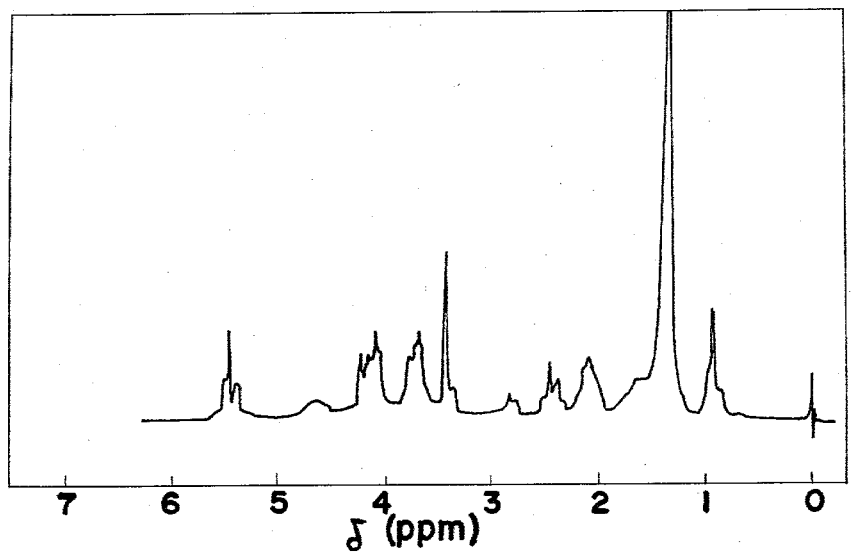

The NMR chart of the said product obtained as in Example 24 is shown in FIG. 25. In the IR spectrum, characteristic absorptions are seen at 1040 and 3430 cm$^{-1}$.

uct having the following structure is obtained as white cream:

EXAMPLE 29

In the same manner as in Example 24, glycidyl t-decanoate (67.7 g; 0.297 mol), sulfur dioxide (19.0 g; 0.297 mol) and dimethylethanolamine (26.4 g; 0.297 mol) are subjected to reaction in the presence of dimethylformamide (35 g) at 70° C., the reaction is completed in 8 hours. The reaction product having the following structure is obtained as reddish brown viscous liquid:

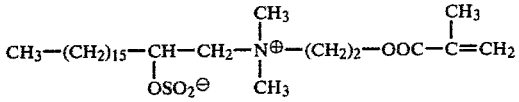

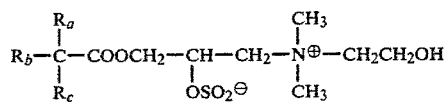

Figure 28:
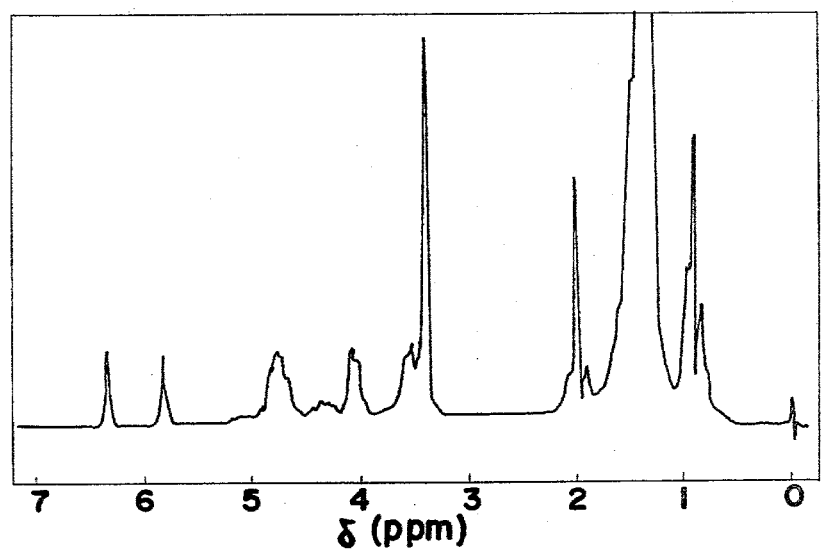

The NMR chart of the said product obtained as in Example 30 is shown in FIG. 28. In the IR spectrum, characteristic absorptions are seen at 1040, 3430 and 1630 cm$^{-1}$.

(wherein $R_1$, $R_b$ and $R_c$ are each alkyl and the total number of the carbon atoms in these alkyls is 8).

Figure 26:
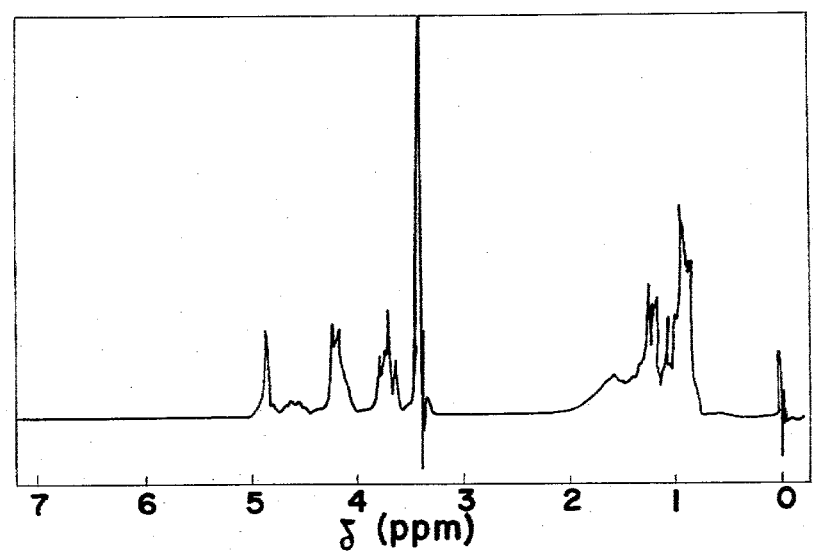

The NMR chart of the said product obtained as in Example 24 is shown in FIG. 26. In the IR spectrum, characteristic absorptions are seen at 1040 and 3430 cm$^{-1}$.

EXAMPLE 32

In the same manner as in Example 30, o-sec-butylphenyl glycidyl ether (84.0 g; 0.408 mol), sulfur dioxide (26.1 g; 0.408 mol) and dimethylaminoethyl methacrylate (64.0 g; 0.408 mol) are subjected to reaction in the presence of hydroquinone (0.1 g) at 70° C., the reaction is completed in 6 hours. The reaction product having the following structure is obtained as white cream:

EXAMPLE 30

In a reactor equipped with a stirrer, 2-ethylhexyl glycidyl ether (81.8 g; 0.44 mol), hydroquinone (0.14 g) and ethyleneglycol monomethyl ether (33.5 g) are charged while cooling at −50° C., and sulfur dioxide (28.2 g; 0.44 mol) is added thereto while maintaining the temperature of the system below −20° C. Then, dimethylaminoethyl methacrylate (69.1 g; 0.44 mol) is introduced therein while maintaining the temperature of the system below −20° C. Thereafter, the tempera-

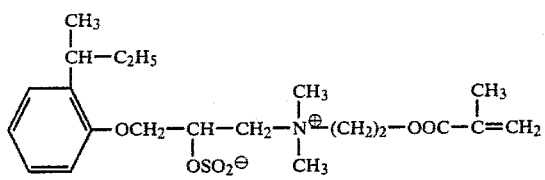

Figure 29:
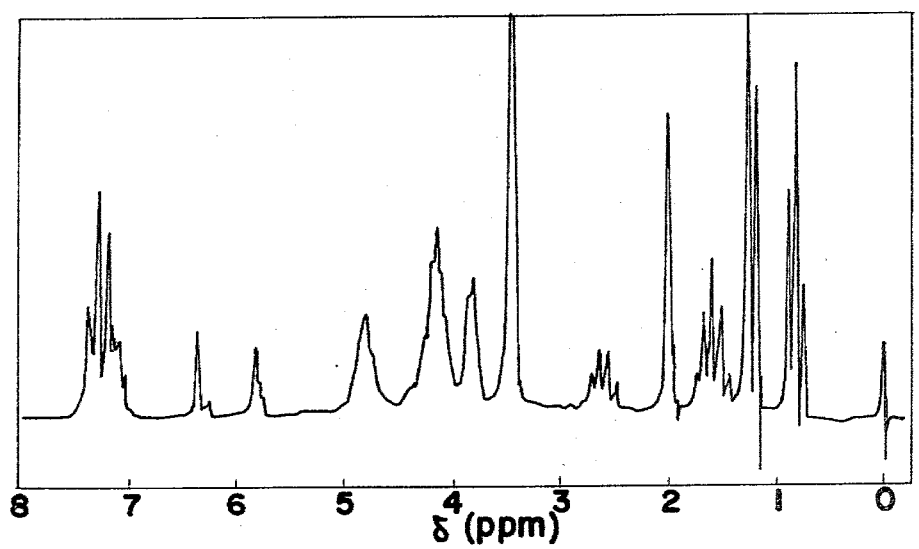

The NMR chart of the said product obtained as in Example 30 is shown in FIG. 29. In the IR spectrum, characteristic absorptions are seen at 1040, 3430 and 1630 cm$^{-1}$.

EXAMPLE 33

In the same manner as in Example 30, glycidyl t-decanoate (155.0 g; 0.68 mol), sulfur dioxide (43.5 g; 0.68 mol) and dimethylaminoethyl methacrylate (106.8 g; 0.68 mol) are subjected to reaction in the presence of hydroquinone (0.2 g) at 70° C., the reaction is completed in 5 hours. The reaction product having the following structure is obtained as yellowish brown cream:

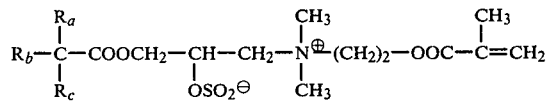

(wherein $R_a$, $R_b$ and $R_c$ are each alkyl and the total number of the carbon atoms in these alkyls is 8).

Figure 30:
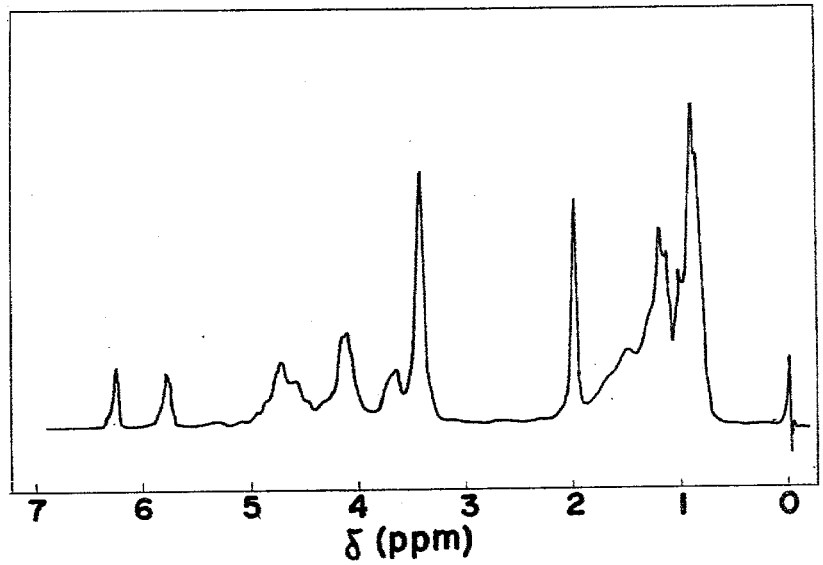

The NMR chart of the said product obtained as in Example 30 is shown in FIG. 30. In the IR spectrum, characteristic absorptions are seen at 1040, 3430 and 1630 cm$^{-1}$.

EXAMPLE 34

In the same manner as in Example 30, glycidyl linoleate (229.0 g; 0.66 mol), sulfur dioxide (42.2 g; 0.66 mol) and dimethylallylamine (56.1 g; 0.66 mol) are subjected to reaction in the presence of hydroquinone (0.1 g) and dimethylformamide (40.0 g) at 70° C., the reaction is completed in 8 hours. The reaction product having the following structure is obtained as yellow cream:

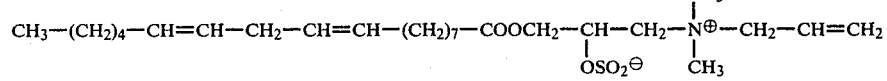

Figure 31:
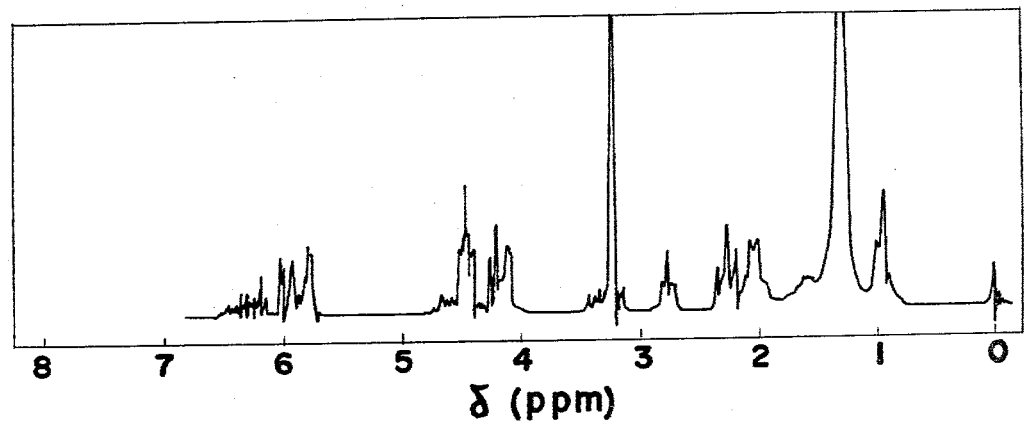

The NMR chart of the said product obtained as in Example 30 is shown in FIG. 31. In the IR spectrum, characteristic absorptions are seen at 1040, 3430 and 1630 cm$^{-1}$.

EXAMPLE 35

In the same manner as in Example 30, icocene oxide (180.4 g; 0.52 mol), sulfur dioxide (33.8 g; 0.52 mol) and dimethylallylamine (44.2 g; 0.52 mol) are subjected to reaction in the pesence of hydroquinone (0.1 g) and to reaction in the presence of hydroquinone (0.1 g) and dimethylformamide (38.0 g) at 70° C., the reaction is completed in 8 hours. The reaction product having the following structure is obtained as yellow cream:

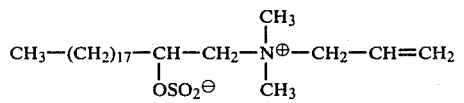

Figure 32:
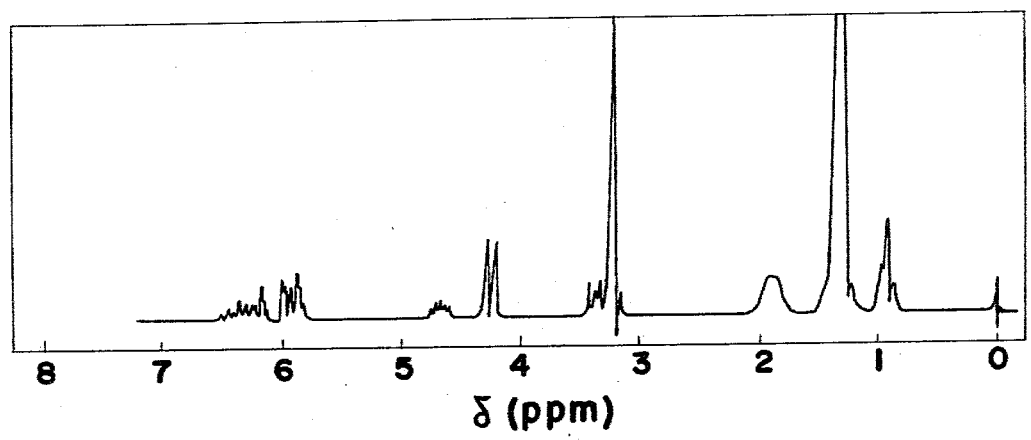

The NMR chart of the said product obtained as in Example 30 is shown in FIG. 32. In the IR spectrum, characteristic absorptions are seen at 1040, 3430 and 1630 cm$^{-1}$.

EXAMPLE 36

In the same manner as in Example 30, 2-ethylhexyl glycidyl ether (102.3 g; 0.55 mol), sulfur dioxide (35.2 g; 0.55 mol) and 4-vinylpyridine (57.8 g; 0.55 mol) are subjected to reaction in the presence of hydroquinone (0.2 g) and ethyleneglycol monomethyl ether (35.0 g) at 70° C., the reaction is completed in 3 hours. The reaction product having the following structure is obtained as yellow cream:

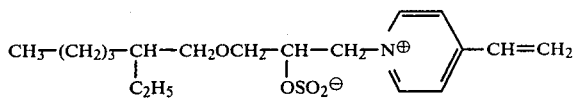

Figure 33:
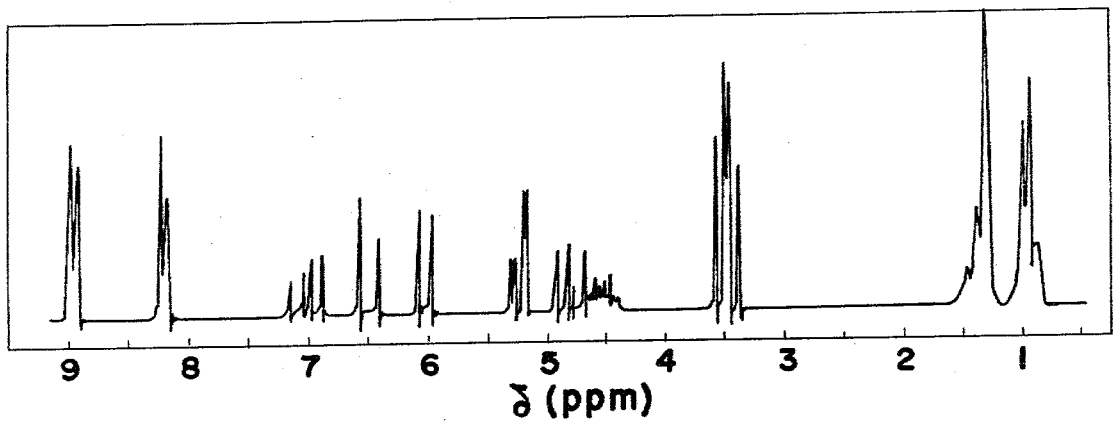

The NMR chart of the said product obtained as in Example 30 is shown in FIG. 33. In the IR spectrum, characteristic absorptions are seen at 1040, 3430 and 1630 cm$^{-1}$.

REFERENCE EXAMPLE 3

In a 2 liter volume reactor equipped with a stirrer, a cooler, a temperature controller and an inlet for nitrogen gas, deionized water (450 g) is charged, and the temperature is elevated up to 80° C. while introducing nitrogen gas therein. Potassium persulfate (4.5 g) and sodium hydrogen sulfite (1.5 g) are charged into the reactor, and the reaction product in Example 30 (20 g), methyl methacrylate (124 g), styrene (125 g), n-butyl methacrylate (166 g), glycidyl methacrylate (60 g) and laurylmercaptan (5 g) are dropwise added thereto in 30 minutes. Further, potassium persulfate (1.5 g), sodium hydrogen sulfite (0.5 g) and deionized water (70 g) are added thereto, and the reaction is continued for 30 minutes, whereby an emulsion of the produced polymer is obtained.

REFERENCE EXAMPLE 4

In a 2 liter volume reactor equipped with a stirrer, a cooler, a temperature controller and an inlet for nitrogen gas, deionized water (408 g) is charged, and the temperature is elevated up to 80° C. while introducing nitrogen gas therein. An aqueous solution of azobiscyanovaleric acid (8 g) and dimethylethanolamine (4.8 g) is charged into the reactor, and the reaction product in Example 31 (16 g), 2-hydroxyethyl acrylate (40 g), methyl methacrylate (103 g), styrene (104 g) and n-butyl acrylate (137 g) are dropwise added thereto in 40 minutes. After the dropwise addition is finished, stirring is continued for 30 minutes, whereby an emulsion of the produced polymer is obtained.

EXAMPLE 37

In a reactor equipped with a stirrer, 2-ethylhexyl glycidyl ether (93 g) and dimethylformamide (88 g) are charged while cooling at −50° C., and sulfur dioxide (32 g) is added thereto while maintaining the temperature of the system below −20° C. Then, dimethylstearylamine (14.85 g) is introduced therein while maintaining the temperature of the system below −20° C. Thereafter, the temperature of the system is gradually elevated up to 80° C. so as to effect the reaction. The reaction is completed in 8 hours. By removal of unreacted materials under reduced pressure, the reaction product having the following structure is obtained as pale yellow paste:

$$CH_3-(CH_2)_3-\underset{\underset{C_2H_5}{|}}{CH}-CH_2-OCH_2-\underset{\underset{OSO_2^\ominus}{|}}{CH}-CH_2-\overset{\overset{CH_3}{|}}{\underset{\underset{CH_3}{|}}{N^\oplus}}-C_{18}H_{37}$$

In the NMR analysis, characteristic peaks are recognized at 3.6 δ and 4.6 δ. In the IR spectrum, characteristic absorptions are seen at 1040 and 3430 cm$^{-1}$.

EXAMPLE 38

In the same manner as in Example 37, 2-ethylhexyl glycidyl ether (93 g), sulfur dioxide (32 g) and N-dodecylmorpholine (127.5 g) are subjected to reaction in the presence of dimethylformamide (85 g) at 80° C., the reaction is completed in 8 hours. The reaction product having the following structure is obtained:

$$C_4H_9-\underset{\underset{C_2H_5}{|}}{CH}-CH_2OCH_2-\underset{\underset{OSO_2^\ominus}{|}}{CH}-CH_2-\overset{\overset{C_{12}H_{25}}{|}}{N^\oplus}\diagdown O$$

In the NMR analysis, characteristic peaks are recognized at 3.6 δ and 4.6 δ. In the IR spectrum, characteristic absorptions are seen at 1040 and 3430 cm$^{-1}$.

EXAMPLE 39

In the same manner as in Example 37, nonylphenyl glycidyl ether (138 g), sulfur dioxide (32 g) and dimethyllaurylamine (106.5 g) are subjected to reaction in the presence of ethyleneglycol monomethyl ether (100 g) at 80° C., the reaction is completed in 8 hours. The reaction product having the following structure is obtained as white transparent viscous liquid:

$$C_9H_{19}-\text{C}_6H_4-OCH_2-\underset{\underset{OSO_2^\ominus}{|}}{CH}-CH_2-\overset{\overset{CH_3}{|}}{\underset{\underset{CH_3}{|}}{N^\oplus}}-C_{12}H_{25}$$

In the NMR analysis, characteristic peaks are recognized at 3.6 δ and 4.6 δ. In the IR spectrum, characteristic absorptions are seen at 1040 and 3430 cm$^{-1}$.

EXAMPLE 40

In the same manner as in Example 37, tetradecene oxide (106 g), sulfur dioxide (32 g) and dimethylstearylamine (148.5 g) are subjected to reaction in the presence of dimethylformamide (100 g) at 80° C. The reaction is completed in 8 hours. The reaction product having the following structure is obtained:

$$C_{12}H_{25}-\underset{\underset{OSO_2^\ominus}{|}}{CH}-CH_2-\overset{\overset{CH_3}{|}}{\underset{\underset{CH_3}{|}}{N^\oplus}}-C_{18}H_{37}$$

In the NMR analysis, characteristic peaks are recognized at 3.6 δ and 4.6 δ. In the IR spectrum, characteristic absorptions are seen at 1040 and 3430 cm$^{-1}$.

EXAMPLE 41

In the same manner as in Example 37, tetradecene oxide (106 g), sulfur oxide (32 g) and 2-hydroxyhexadecyldimethylamine (156.5 g) are subjected to reaction in the presence of dimethylformamide (100 g) at 80° C. The reaction is completed in 8 hours. The reaction product having the following structure is obtained:

$$C_{12}H_{25}-\underset{\underset{OSO_2^\ominus}{|}}{CH}-CH_2-\overset{\overset{CH_3}{|}}{\underset{\underset{CH_3}{|}}{N^\oplus}}-CH_2-\underset{\underset{OH}{|}}{CH}-C_{14}H_{29}.$$

In the NMR analysis, characteristic peaks are recognized at 3.6 δ and 4.6 δ. In the IR spectrum, characteristic absorptions are seen at 1040 and 3430 cm$^{-1}$.

EXAMPLE 42

In the same manner as in Example 37, glycidyl linoleate (173.5 g), sulfur dioxide (32 g) and 2-hydroxydodecyldimethylamine (114.5 g) are subjected to reaction in the presence of dimethylformamide (110 g) at 80° C. The reaction is completed in 8 hours. The reaction product having the following structure is obtained:

$$CH_3(CH_2)_4CH=CHCH_2CH=CH(CH_2)_7-COO-CH_2\underset{\underset{OSO_2^\ominus}{|}}{CH}-CH_2-\overset{\overset{CH_3}{|}}{\underset{\underset{CH_3}{|}}{N^\oplus}}-CH_2-\underset{\underset{OH}{|}}{CH}-C_{10}H_{21}$$

In the NMR analysis, characteristic peaks are recognized at 3.6 δ and 4.6 δ. In the IR spectrum, characteristic absorptions are seen at 1040 and 3430 cm$^{-1}$.

EXAMPLE 43

In the same manner as in Example 37, glycidyl t-decanoate (114 g), sulfur dioxide (32 g) and dimethyllaurylamine 106.5 g) are subjected to reaction in the presence of dimethylformamide (88 g) at 80° C. The reaction is completed in 8 hours. The reaction product having the following structure is obtained:

$$R_b-\underset{\underset{R_c}{|}}{\overset{\overset{R_a}{|}}{C}}-COO-CH_2-\underset{\underset{OSO_2^\ominus}{|}}{CH}-CH_2-\overset{\overset{CH_3}{|}}{\underset{\underset{CH_3}{|}}{N^\oplus}}-C_{12}H_{25}$$

(wherein $R_a$, $R_b$ and $R_c$ are each alkyl and the total number of the carbon atoms in these alkyls is 8).

In the NMR analysis, characteristic peaks are recognized at 3.6 δ and 4.6 δ. In the IR spectrum, characteristic absorptions are seen at 1040 and 3430 cm$^{-1}$.

What is claimed is:

1. A process for preparing an ampho-ionic compound of the formula:

$$R-\underset{\underset{OSO_2^\ominus}{|}}{\overset{\overset{R_2}{|}}{C}}-CH_2-B^\oplus$$

wherein R is a group of the formula:

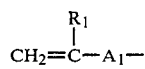

wherein $R_1$ is hydrogen or methyl and $A_1$ is —COOCH$_2$—, —CH$_2$OCH$_2$— or —CONHCH$_2$—;
$R_2$ is hydrogen or methyl; and
$B^\oplus$ is a group of any one of the formulas:

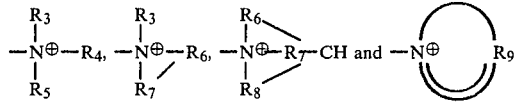

wherein $R_3$, $R_4$ and $R_5$ are each alkyl, alkenyl, hydroxyalkyl, mercaptoalkyl, alkoxy, alkylthio, cyclic alkyl, phenyl or substituted phenyl, each of these groups having not more than 7 carbon atoms, $R_6$, $R_7$ and $R_8$ are each alkylene, alkenylene, alkyleneoxy or alkylenethio, each of these groups having not more than 7 carbon atoms, and $R_9$ is optionally substituted alkylidene of 4 to 10 carbon atoms, which comprises reacting a compound of the formula:

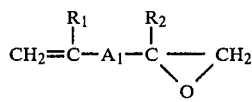

wherein $R_1$, $R_2$ and $A_1$ are each as defined above, with sulfur dioxide and a tertiary amine of any one of the formulas:

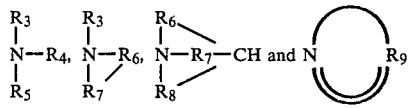

wherein $R_3$, $R_4$, $R_5$, $R_6$, $R_7$, $R_8$ and $R_9$ are each as defined above.

2. A process for preparing an ampho-ionic compound of the formula:

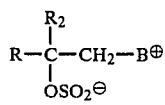

wherein R is a group of the formula:

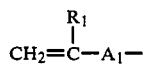

wherein $R_1$ is hydrogen or methyl and $A_1$ is —COOCH$_2$—, —CH$_2$OCH$_2$— or —CONHCH$_2$—;
$R_2$ is hydrogen or methyl; and
$B^\oplus$ is a group of the formula:

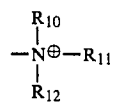

wherein $R_{10}$, $R_{11}$ and $R_{12}$ are each a substituent comprising as the major constituent a hydrocarbon chain having 10 to 30 carbon atoms, or when two or three of them are combined together, they represent a heterocyclic group,
which comprises reacting a compound of the formula:

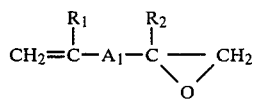

wherein $R_1$, $R_2$ and $A_1$ are each as defined above, with sulfur dioxide and a tertiary amine of the formula:

wherein $R_{10}$, $R_{11}$ and $R_{12}$ are each as defined above.

3. A process for preparing an ampho-ionic compound of the formula:

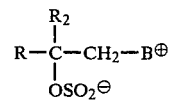

wherein R is a group of the formula:

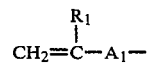

wherein $R_1$ is hydrogen or methyl and $A_1$ is —COOCH$_2$—, —CH$_2$OCH$_2$— or —CONHCH$_2$—;
$R_2$ is hydrogen or methyl; and
$B^\oplus$ is a group of the formula:

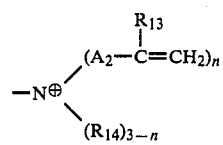

wherein $R_{13}$ is hydrogen or methyl, $R_{14}$ is a substituent comprising as the major constituent a hydrocarbon chain having 1 to 20 carbon atoms, $A_2$ is —(CH$_2$)$_m$OCH—, —(CH$_2$)$_m$NHCO— or —(CH$_2$)$_m$—, or when taken together with a part or the whole of $R_{14}$, forms a heterocyclic structure, m is an integer of 1 to 4 and n is an integer of 1 to 3,
which comprises reacting a compound of the formula:

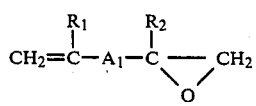

wherein $R_1$, $R_2$ and $A_1$ are each as defined above, with sulfur dioxide and a tertiary amine of the formula:

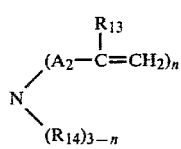

wherein $R_{13}$, $R_{14}$, $A_2$ and n are each as defined above.

4. A process for preparing an ampho-ionic compound of the formula:

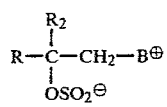

wherein R is a substituent comprising as the major constituent a hydrocarbon chain having 8 to 30 carbon atoms;
$R_2$ is hydrogen or methyl; and
$B^\oplus$ is a group of the formula:

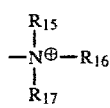

wherein $R_{15}$, $R_{16}$, $R_{17}$ are each a substituent comprising as the major constituent a hydrocarbon group having 3 to 8 carbon atoms and possessing no polymerizability, or when two or three of them are combined together, they represent a heterocyclic group,
which comprises reacting a compound of the formula:

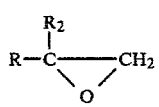

wherein R and $R_2$ are each as defined above, with sulfur dioxide and a tertiary amine of the formula:

wherein $R_{15}$, $R_{16}$ and $R_{17}$ are each as defined above.

5. A process for preparing an ampho-ionic compound of the formula:

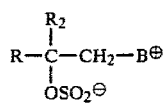

wherein R is a substituent comprising as the major constituent a hydrocarbon chain having 8 to 30 carbon atoms;
$R_2$ is hydrogen or methyl; and
$B^\oplus$ is a group of the formula:

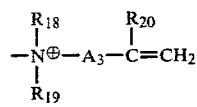

wherein $R_{18}$ and $R_{19}$ are each a substituent comprising as the major constituent a hydrocarbon group having 2 to 7 carbon atoms, $R_{20}$ is hydrogen or methyl and $A_3$ is $-COO(CH_2)_p-$, $-CONH(CH_2)_p-$ or $-(CH_2)_p-$, or when taken together with $R_{18}$ or with $R_{18}$ and $R_{19}$, forms a heterocyclic structure, and p is an integer of 1 to 3,
which comprises reacting a compound of the formula:

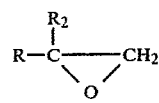

wherein R and $R_2$ are each as defined above, with sulfur dioxide and a tertiary amine of the formula:

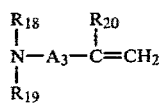

wherein $R_{18}$, $R_{19}$, $R_{20}$ and $A_3$ are each as defined above.

6. A process for preparing an ampho-ionic compound of the formula:

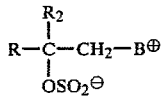

wherein R is a substituent comprising as the major constituent a hydrocarbon chain having 8 to 30 carbon atoms;
$R_2$ is hydrogen or methyl; and
$B^\oplus$ is a group of the formula:

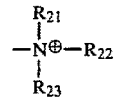

wherein $R_{21}$, $R_{22}$ and $R_{23}$ are each a substituent comprising as the major constituent a hydrocarbon chain having 10 to 30 carbon atoms, or when two or three of them are taken together, they represent a heterocyclic group,
which comprises reacting a compound of the formula:

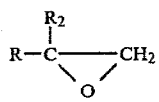

wherein R and $R_2$ are each as defined above, with sulfur dioxide and a tertiary amine of the formula:

wherein $R_{21}$, $R_{22}$ and $R_{23}$ are each as defined above.

* * * * *